(12) United States Patent
Lee et al.

(10) Patent No.: US 9,277,930 B2
(45) Date of Patent: Mar. 8, 2016

(54) INTERVERTEBRAL DISC REPLACEMENT AND ASSOCIATED INSTRUMENTATION

(71) Applicant: K2M, Inc., Leesburg, VA (US)

(72) Inventors: Casey K. Lee, Florham Park, NJ (US); George Makris, West Orange, NJ (US); Alastair J. T. Clemow, Princeton, NJ (US)

(73) Assignee: K2M, Inc., Leesburg, VA (US)

( * ) Notice: Subject to any disclaimer, the term of this patent is extended or adjusted under 35 U.S.C. 154(b) by 0 days.

(21) Appl. No.: 14/455,815

(22) Filed: Aug. 8, 2014

(65) Prior Publication Data

US 2014/0350560 A1    Nov. 27, 2014

Related U.S. Application Data

(62) Division of application No. 12/091,296, filed as application No. PCT/US2006/041540 on Oct. 24, 2006, now Pat. No. 8,814,938.

(60) Provisional application No. 60/759,987, filed on Jan. 19, 2006, provisional application No. 60/729,241, filed on Oct. 24, 2005.

(51) Int. Cl.
*A61B 17/16* (2006.01)
*A61B 17/17* (2006.01)
*A61F 2/44* (2006.01)
*A61F 2/30* (2006.01)

(52) U.S. Cl.
CPC ......... *A61B 17/1757* (2013.01); *A61B 17/1642* (2013.01); *A61B 17/1671* (2013.01); *A61F 2/44* (2013.01); *A61B 17/1659* (2013.01); *A61B 2017/1602* (2013.01); *A61F 2002/30841* (2013.01); *A61F 2002/30884* (2013.01)

(58) Field of Classification Search
CPC ........... A61B 17/1757; A61B 17/1642; A61B 17/1671
See application file for complete search history.

(56) References Cited

U.S. PATENT DOCUMENTS

| 3,867,728 A | 2/1975 | Stubstad et al. |
| 3,875,595 A | 4/1975 | Froning |
| 4,349,921 A | 9/1982 | Kuntz |

(Continued)

FOREIGN PATENT DOCUMENTS

| DE | 42 19 939 A1 | 12/1993 |
| DE | 201 11 479 U1 | 11/2001 |

(Continued)

OTHER PUBLICATIONS

Hellier WG et al., Spine 1992, 127(6 Suppl.): Ss86-96.

(Continued)

*Primary Examiner* — Christian Sevilla
(74) *Attorney, Agent, or Firm* — Carter, DeLuca, Farrell & Schmidt, LLP

(57) ABSTRACT

An endplate for an intervertebral prosthesis includes an inner domed region and a peripheral rim wherein the inner domed region has a non-circular plan and has an area that is at least 50% of the area of the endplate. A surgical instrument for milling a recess in a vertebral endplate includes a cutting tool having a drive shaft with a positioning collar, a guard frame, and a pair of guide plates attached to the guard frame and spaced to confine the positioning collar and having guide slots for the drive shaft.

11 Claims, 37 Drawing Sheets

(56) References Cited

U.S. PATENT DOCUMENTS

| | | |
|---|---|---|
| 4,759,766 A | 7/1988 | Buttner-Janz |
| 4,759,769 A | 7/1988 | Hedman |
| 4,772,287 A | 9/1988 | Ray et al. |
| 4,863,477 A | 9/1989 | Monson |
| 4,904,260 A | 2/1990 | Ray et al. |
| 4,911,718 A | 3/1990 | Lee et al. |
| 4,932,969 A | 6/1990 | Frey et al. |
| 4,946,378 A | 8/1990 | Hirayama et al. |
| 5,047,055 A | 9/1991 | Baa et al. |
| 5,071,437 A | 12/1991 | Steffee |
| 5,123,926 A | 6/1992 | Pisharodi |
| 5,171,281 A | 12/1992 | Parsons et al. |
| 5,190,547 A | 3/1993 | Barber et al. |
| 5,192,326 A | 3/1993 | Bao et al. |
| 5,258,031 A | 11/1993 | Salib et al. |
| 5,306,308 A | 4/1994 | Gross et al. |
| 5,306,309 A | 4/1994 | Wagner et al. |
| 5,314,477 A | 5/1994 | Marnay |
| 5,320,644 A | 6/1994 | Baumgartner |
| 5,370,697 A | 12/1994 | Baumgartner |
| 5,401,269 A | 3/1995 | Buttner-Janz et al. |
| 5,458,642 A | 10/1995 | Beer et al. |
| 5,484,437 A * | 1/1996 | Michelson ......... A61B 17/1671 128/898 |
| 5,514,180 A | 5/1996 | Heggeness et al. |
| 5,534,028 A | 7/1996 | Bao et al. |
| 5,534,030 A | 7/1996 | Navarro et al. |
| 5,545,229 A | 8/1996 | Parsons et al. |
| 5,556,431 A | 9/1996 | Buttner-Janz |
| 5,562,738 A | 10/1996 | Boyd et al. |
| 5,674,294 A | 10/1997 | Bainville et al. |
| 5,674,296 A | 10/1997 | Bryan et al. |
| 5,676,702 A | 10/1997 | Ratron |
| 5,683,465 A | 11/1997 | Shinne et al. |
| 5,824,093 A | 10/1998 | Ray et al. |
| 5,824,094 A | 10/1998 | Serhan et al. |
| 5,865,846 A | 2/1999 | Bryan et al. |
| 5,888,226 A | 3/1999 | Rogozinski |
| 5,893,889 A | 4/1999 | Harrington |
| 5,976,186 A | 11/1999 | Bao et al. |
| 6,113,637 A | 9/2000 | Gill et al. |
| 6,136,031 A | 10/2000 | Middleton |
| 6,139,579 A | 10/2000 | Steffee |
| 6,156,067 A | 12/2000 | Bryan et al. |
| 6,162,252 A | 12/2000 | Kuras et al. |
| 6,187,043 B1 | 2/2001 | Ledergerber |
| 6,187,048 B1 | 2/2001 | Milner et al. |
| 6,224,607 B1 | 5/2001 | Michelson |
| 6,296,664 B1 | 10/2001 | Middleton |
| 6,315,797 B1 | 11/2001 | Middleton |
| 6,348,071 B1 | 2/2002 | Steffee et al. |
| 6,368,350 B1 | 4/2002 | Erickson et al. |
| 6,395,032 B1 | 5/2002 | Gauchet |
| 6,419,704 B1 | 7/2002 | Ferree |
| 6,419,706 B1 | 7/2002 | Graf |
| 6,482,234 B1 | 11/2002 | Weber et al. |
| 6,527,804 B1 | 3/2003 | Gauchet et al. |
| 6,533,818 B1 | 3/2003 | Weber et al. |
| 6,579,320 B1 | 6/2003 | Gauchet et al. |
| 6,579,321 B1 | 6/2003 | Gordon et al. |
| 6,582,466 B1 | 6/2003 | Gauchet |
| 6,582,467 B1 | 6/2003 | Teitelbaum et al. |
| 6,582,468 B1 | 6/2003 | Gauchet |
| 6,592,624 B1 | 7/2003 | Fraser et al. |
| 6,607,558 B2 | 8/2003 | Kuras |
| 6,626,943 B2 | 9/2003 | Eberlein |
| 6,645,248 B2 | 11/2003 | Casutt |
| 6,656,224 B2 | 12/2003 | Middleton |
| 6,669,732 B2 | 12/2003 | Serhan et al. |
| 6,682,562 B2 | 1/2004 | Viart et al. |
| 6,726,720 B2 | 4/2004 | Ross et al. |
| 6,733,532 B1 | 5/2004 | Gauchet |
| 6,740,118 B2 | 5/2004 | Eisermann |
| 6,749,635 B1 | 6/2004 | Bryan |
| 6,893,465 B2 | 5/2005 | Huang |
| 7,169,181 B2 | 1/2007 | Kuras |
| 7,250,060 B2 | 7/2007 | Trieu |
| 2001/0016773 A1 | 8/2001 | Serhan et al. |
| 2001/0032017 A1 | 10/2001 | Alfaro |
| 2001/0051829 A1 | 12/2001 | Middleton |
| 2002/0022888 A1 | 2/2002 | Serhan et al. |
| 2002/0077533 A1 | 6/2002 | Sieger et al. |
| 2002/0077701 A1 | 6/2002 | Kuslich |
| 2003/0045939 A1 | 3/2003 | Casutt |
| 2003/0074066 A1 | 4/2003 | Errico |
| 2003/0100951 A1 | 5/2003 | Serhan et al. |
| 2003/0135277 A1 | 7/2003 | Bryan |
| 2003/0164172 A1 | 9/2003 | Chumas et al. |
| 2003/0208271 A1 | 11/2003 | Kuras |
| 2003/0236526 A1 | 12/2003 | Van Hoeck |
| 2004/0002711 A1 | 1/2004 | Berry |
| 2004/0103903 A1 | 6/2004 | Falahee |
| 2004/0122517 A1 | 6/2004 | Kuras et al. |
| 2004/0122518 A1 | 6/2004 | Rhoda |
| 2004/0143332 A1 | 7/2004 | Krueger et al. |
| 2004/0162563 A1 | 8/2004 | Michelson |
| 2004/0167626 A1 | 8/2004 | Geremakis |
| 2004/0193273 A1 | 9/2004 | Huang |
| 2004/0215197 A1 | 10/2004 | Smith et al. |
| 2004/0220668 A1 | 11/2004 | Eisermann et al. |
| 2004/0249462 A1 | 12/2004 | Huang |
| 2004/0267367 A1 | 12/2004 | O'Neil |
| 2005/0027300 A1 | 2/2005 | Hawkins et al. |
| 2005/0131544 A1 | 6/2005 | Kuras |
| 2005/0273111 A1 | 12/2005 | Ferree |
| 2006/0079907 A1 | 4/2006 | Boettiger |
| 2006/0229724 A1 | 10/2006 | Lechmann |
| 2006/0265075 A1 | 11/2006 | Baumgartner |
| 2006/0276900 A1 | 12/2006 | Carpenter |

FOREIGN PATENT DOCUMENTS

| | | | |
|---|---|---|---|
| EP | 0 566 810 A1 | | 10/1993 |
| EP | 0 642 775 A1 | | 3/1995 |
| FR | 2 784 291 A1 | | 4/2000 |
| GB | 1 496 804 | | 1/1978 |
| GB | 1 589 192 | | 5/1981 |
| WO | WO 89/03663 A1 | | 5/1989 |
| WO | WO 90/11740 A1 | | 10/1990 |
| WO | WO 95/19153 A1 | | 7/1995 |
| WO | WO 99/22675 A1 | | 4/1999 |
| WO | WO 01/60232 | * | 12/2001 |
| WO | WO 03/090650 A1 | | 11/2003 |
| WO | WO 2004/033516 A1 | | 4/2004 |
| WO | WO 2004/039291 A1 | | 5/2004 |
| WO | WO 2004/054453 A1 | | 7/2004 |
| WO | WO 2005/072660 A1 | | 8/2005 |
| WO | WO 2005/007041 A1 | | 12/2005 |

OTHER PUBLICATIONS

Fraser RD et al., Spine J. 2004, 4(6S): 245s-251s.
Szpalski M, Eur. Spine J. (2000), 11 (Suppl.2): S65-84.
McAfee, P. et al., Spine J. 4:48s, 2004.
Hawkins MV et al., J. Orthop. Res. 12: 119-127, 1994.
Closkey RF et al., Spine 18(8): 1011-1015, 1993.
Langrana NA et ai.,Spine J. 4 (2004), 245S-251S.

* cited by examiner

INTERVERTEBRAL DISC REPLACEMENT AND ASSOCIATED INSTRUMENTATION

CROSS REFERENCE TO RELATED APPLICATIONS

This application claims the benefit of U.S. Provisional Application No. 60/729,241, filed Oct. 24, 2005, the entire disclosure of which is incorporated herein by reference, and the benefit of U.S. Provisional Application No. 60/759,987, filed Jan. 19, 2006, the entire disclosure of which is incorporated herein by reference.

BACKGROUND OF THE INVENTION

1. Field of the Invention

This invention relates to prostheses for replacing intervertebral discs of the human spine and more particularly to endplates for intervertebral disc prostheses having a central domed region and a peripheral rim. The invention also relates to surgical instruments for preparing a vertebra to receive an intervertebral disc prosthesis.

2. Background Art

The most common pathologic condition causing chronic low back pain and neck pain is degenerative disc disease. Disc excision, decompression, and/or spinal fusion have been surgical procedures commonly performed on patients with degenerative disc disease when non-operative treatment fails to relieve chronic disabling pain. More recently, replacement of a degenerated disc with an artificial disc prosthesis has become an available choice for pain relief and restoring function.

For successful results from disc arthroplasty, it is desirable that a prosthesis for implantation in the intervertebral space include structures disposed and configured to promote the proper positioning, alignment and immediate post-operative stability of the prosthesis within the intervertebral space. Post-operative stability is important since a disc prosthesis that is not securely stabilized within the disc space may result in accelerated disc degeneration, the formation of osteophytes, and subsidence into the vertebrae, leading to a loss in disc height. The occurrence of such subsidence is in turn affected by three factors: (i) the applied load upon the device, (ii) the quality, or bone mineral density, of the vertebra and (iii) the contact surface area between the prosthesis and the bone. The vertebral endplates of the normal human lumbar-sacral spine have a wide range of variable contours and curvatures. However, in general, they have a concave curvature, with a rim of dense compact or cortical bone and a central region of cancellous bone.

Accordingly, flat prosthetic endplate designs are prone to have problems of incongruous fit between the prosthetic endplate and the vertebral endplate due to mismatched shape, and may not provide post-operative stability of the prosthesis in the disc space. A number of disc prostheses having flat endplates incorporate additional mechanisms of fixation to bone by screws, spikes, keels, or serrated surfaces. Some of such mechanisms may require excessive distraction of the adjacent vertebrae in order to provide sufficient intervertebral disc space for insertion. Such a procedure may damage adjacent tissues or even result in fracture of the vertebral bone.

Other prosthesis endplate designs having somewhat convex surfaces may provide a better match for the generally concave contours of the vertebral endplates. However, the terminal surfaces of the vertebrae do not have a simple geometrical shape, and vary from patient to patient. Various methods of shaping the vertebral endplates to accommodate the matching endplates of an intervertebral prosthesis have been proposed. However, a need has continued to exist for an intervertebral prosthesis endplate that can be readily fitted to the vertebrae of a patient with simple and accurate adaptation of the prosthesis endplate to the vertebral endplate, thereby providing a relatively large contact area between the prosthesis endplate and the vertebral endplate with concomitant good stability of the prosthesis within the intervertebral space.

Proper preparation of the vertebral endplates during disc replacement surgery is an important element of the procedure that can affect the clinical outcome of the surgery. It is desirable that the instruments provide an accurate means of shaping the endplates to receive the implant without damaging adjacent structures. Various instruments have been disclosed or utilized, but many suffer from the disadvantage that they damage or remove some of the peripheral bony rim in order to reach the endplate. The result is that the implant receives less than optimum support from the remaining compact bone, leading to higher interfacial contact stresses and an increased potential for expulsion. It is also desirable that the instruments for preparing the vertebral endplates be easy to use.

Accordingly, a need has also continued to exist for instruments and procedures for preparing a seat in the vertebral endplate to receive a complementary structure on the prosthesis endplate.

SUMMARY OF THE INVENTION

According to an exemplary implementation of the invention, an endplate for an intervertebral prosthesis is provided which includes:
  an inner domed region configured and disposed to contact a prepared recess in an endplate of a vertebra, and
  a peripheral rim configured and disposed to contact an intact peripheral rim of the vertebra wherein the peripheral rim substantially surrounds the inner domed region, the circumference of the peripheral rim defining the area of the endplate,
  wherein the inner domed region has a non-circular base periphery joined to the peripheral rim and defining an area of the domed region with the surface of the domed region rising above the peripheral rim, and
  the area of the domed region comprises at least 50% of the area of the endplate.

According to another exemplary implementation of the invention, an instrument for milling a recess in a vertebral endplate for receiving a complementary structure on an endplate of an intervertebral disc prosthesis includes:
  a surgical cutting tool including a surgical cutter and a drive shaft attached thereto and a guide collar positioned on the drive shaft; and
  a guide frame for positioning and guiding the surgical cutter in an intervertebral space between two adjacent vertebrae along a spinal axis for milling an endplate of at least one of the vertebrae,
  wherein the guide frame comprises a first guide plate adapted to be fixed to at least one of the vertebrae, and the guide plate has a first generally central aperture sized for admitting the drive shaft and at least one guide slot communicating with the central aperture and adapted to guide the drive shaft in a predetermined path, and
  a second guide plate, oriented parallel to the first guide plate and spaced anteriorly therefrom a distance selected to confine the guide collar between the first and second guide plates with the drive shaft oriented generally perpendicularly to the guide plates, the second guide plate having a second generally central aperture sized for admitting the drive shaft and at least one guide slot communicating with the central aperture and adapted to guide the drive shaft in a predetermined path.

Accordingly, in one aspect, the invention provides an intervertebral disc prosthesis that has at least one endplate with a dome that provides for torsional and extrusion stability.

In another aspect, the invention provides a prosthesis endplate having a rim for generally congruent contact with the rim of a vertebral body endplate and a domed region for congruent contact with a recess prepared in the vertebral endplate.

In another aspect, the invention provides an intervertebral disc prosthesis that allows reliable and easy positioning, alignment, preparation of a congruent contact surface, and better stabilization against axial, bending, torsion and translation forces in the lumbar, lumbosacral, or cervical spine.

In another aspect, the invention provides an intervertebral prosthesis that addresses the problems of limited accessibility, difficult surgical exposure and maintenance of collateral anatomical structures.

In a further aspect, the invention provides instrumentation that allows the formation of the desired concavity on the vertebral endplate to accept the complementary domed prosthesis endplate.

Further aspects of the invention will become apparent from the description of the invention which follows.

DETAILED DESCRIPTION OF THE INVENTION AND PREFERRED EMBODIMENTS

Figure 1A:
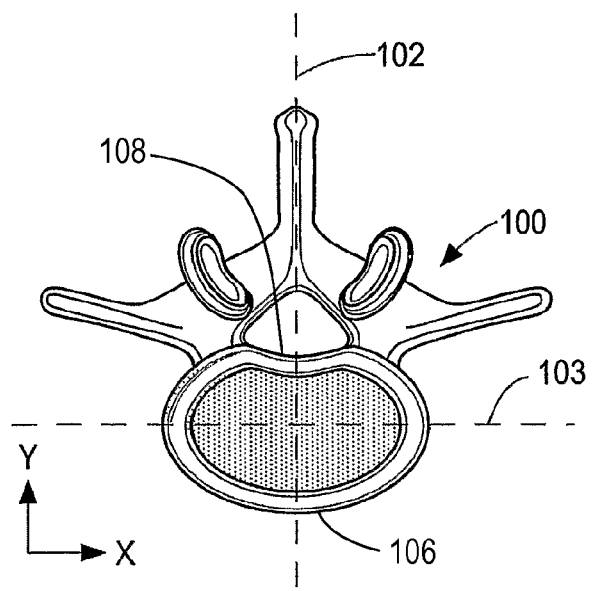
FIGS. 1A, 1B, and 1C illustrate orthogonal planes of a vertebra relevant to the invention of this application.

A vertebral body endplate of a human patient exhibits a peripheral rim region and a central region. According to the invention, a prosthesis endplate is provided that can achieve congruent contact with both the peripheral rim region of the vertebral endplate and the central region of the vertebral endplate.

In one embodiment of the invention, an artificial intervertebral disc prosthesis is constructed from a biocompatible material or materials, having endplates on both its superior and inferior surfaces which provide for secure attachment of the device to the adjacent vertebrae. These prosthesis endplates have a dome-shaped inner region disposed and configured to fit into a prepared recess or cavity in the underlying vertebral bone and a peripheral rim disposed and configured to provide generally congruent contact with the peripheral rim region of the vertebral endplate. Furthermore, the plan of the domed region has a non-circular configuration in order to provide good resistance against relative movement of the intervertebral prosthesis and adjacent vertebral endplate caused by torsional stresses imposed on the vertebral endplate, e.g., by rotational movement of the spine of the patient.

In the description of the prosthesis endplate according to the invention presented in this application the skilled practitioner will understand that an intervertebral prosthesis will generally be provided with an upper and a lower endplate. The domed region of each endplate is positioned to interact with the vertebral endplate of the adjacent vertebra. Accordingly, the domed region of the upper prosthesis endplate, which contacts the lower vertebral endplate of the cephalad vertebra will extend in a generally upward or cranial direction, while the domed region of the lower prosthesis endplate, which contacts the upper vertebral endplate of the caudad vertebra will extend in a generally downward or caudal direction. The description of the endplate according to the invention which follows will generally refer to the domed region as extending upward and the configuration of the domed region in a transverse plane as a plan or superior view. Such a description is not to be interpreted as limiting the endplate of the invention to one particular orientation of the prosthesis endplate of the invention, for a prosthesis endplate of a given configuration can be employed either as an upper endplate of a prosthesis or, mutatis mutandis, as a lower endplate of a prosthesis.

Thus, the dome-with-rim configuration provides close contact of the prosthesis endplate with the adjacent vertebral endplate in order to resist relative motion of the prosthesis endplate and vertebral endplate under the compressive, bending and torsional forces encountered during normal daily activities. The non-circular plan shape of the domed region tends to provide greater resistance to these forces than can be achieved with a circular dome or a simple flat surface. In one aspect, the shape of the dome, when viewed from above, can be generally rectangular in form, optionally with rounded corners, while in another embodiment the shape may be oval. Other alternate shapes include square and more complex shapes. The stability of the domed prosthesis endplate with respect to the adjacent vertebral endplate can be further enhanced by providing additional features on the vertebra-contacting surface of the domed region and/or the rim, such as small protrusions, fins, spike wedges and the like, which fit into recesses in the bone and resist relative motion between the vertebra and the prosthesis endplate. Furthermore, the vertebra-contacting (or outer) surface of the prosthesis can be provided with a roughened or beaded surface, or the like, to allow bone ingrowth.

Figure 7A:
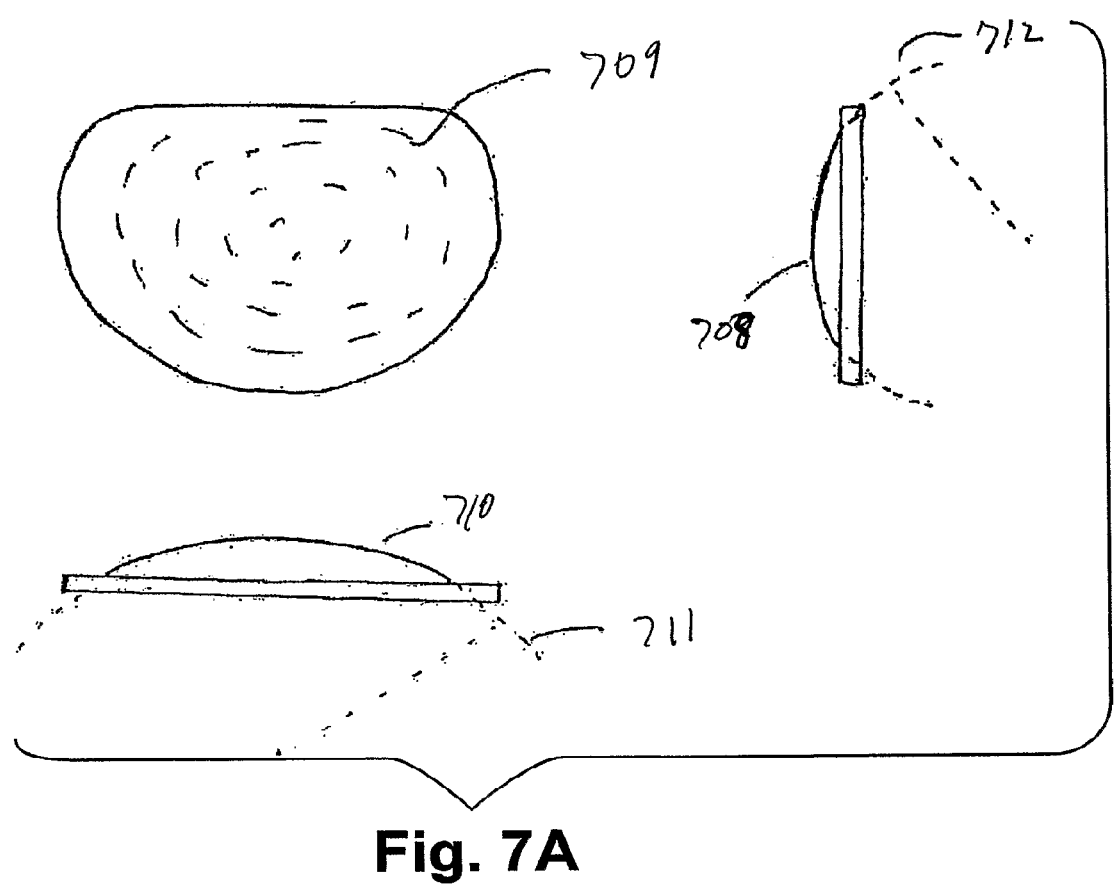
FIG. 7A illustrates a further embodiment of the prosthesis endplate of the invention.

In another embodiment, best seen in FIG. 7A, an artificial disc prosthesis is constructed from a biocompatible material or materials, having endplates on both its superior and inferior surfaces which provide for secure attachment of the device to the adjacent vertebrae. These endplates have an inner domed region shaped to fit into prepared cavities in the underlying vertebral bone, and a peripheral rim, except that in this embodiment the dome has a generally oval or elliptical plan form by reason of having different radii of curvatures in its coronal and saggital planes. Thus, by adjusting the centers of curvature of the domed region in the sagittal and coronal planes the domed region can be configured to have a vertex or peak located either generally at the center of the prosthetic endplate or displaced from the center in an anterior, posterior, lateral or other direction. In any case, the generally oval plan shape of the domed region, as well as any asymmetry in positioning of a vertex or peak of the domed region, provides for greater stability of the device and resistance to expulsion. In the same way as for the first embodiment, the stability of the dome can be further increased with mechanical fixation features such as fins and spikes, as well as by texturing the outer surface. In this embodiment also, the rim, which may be generally flat, rests upon the outer or peripheral rim of cortical bone in the vertebra and provides for efficient load transfer to the strongest region of bone. The combination of rim and dome provides stability of the prosthesis under normal daily activity.

The present invention also provides appropriate instruments for preparing the vertebral endplates to receive the domed prosthesis endplates of the invention. Since it is desired to prepare the endplates without damaging or removing the peripheral vertebral rim, it is important that only the central portion of the vertebral endplate be milled or sculpted to receive the domed inner region of the prosthesis endplate of the invention. Prior art in this area describes instruments which are capable of machining the vertebral endplates, but all do so at the expense of at least a part of the peripheral rim. Additional prior art teaches the formation of a spherical dome cavity by plunging a spherical forming tool perpendicular to the vertebral endplate central region. However, spherical domes only provide a small level of extrusion stability and very low torsional resistance. The present invention describes instruments which allow the vertebral endplates to be prepared to receive a congruent implant, but without damaging the bony rim.

One embodiment of the invention describes a rasp or equivalent which is made to oscillate by means of either manual or power operation and in so doing removes the appropriate amount of bone in the desired shape. This instrument, manufactured from a suitably biocompatible and strong material such as stainless steel, and formed in the appropriate shape to match the desired implant, is introduced into the disc cavity and behind the bony rim or lip of the vertebral bone following standard discectomy. The instrument is then translated forwards and backwards or from side-to-side as desired to remove the appropriate amount of bone and to form a cavity of desired shape. The advantage of this instrument is that it allows preparation of the endplates without removal of the bony rim and thereby increases the stability of the implant and its resistance to expulsion.

In a further embodiment of a dome forming instrument, a guide channel captures and controls the forming tool position and, by dictating the forming tool, path allows for accurate dome recess cavity formation in size, shape and relative position to the vertebral endplate. The novelty of the dome forming tool and guide permits the formation of a fully recessed dome shape providing anti-extrusion and anti-rotational resistance enhancing implant fixation. Prior technique utilizes a plunging method to introduce the forming tool within the intervertebral cavity resulting in at least partial removal of the anterior rim of the vertebral body. The present invention allows for the tool insertion through the intervertebral opening, and, upon engagement of the guide, the tool is guided in the direction of the vertebral endplate. This is possible with the tool shank having a diameter smaller than the tool diameter, the difference in diameters being at least double the maximum depth of the dome recess that is to be formed.

The invention will now be described with reference to the accompanying drawings, wherein the illustrated embodiments are to be considered as illustrative and not limiting, the invention being defined by the appended claims.

Figure 1C:
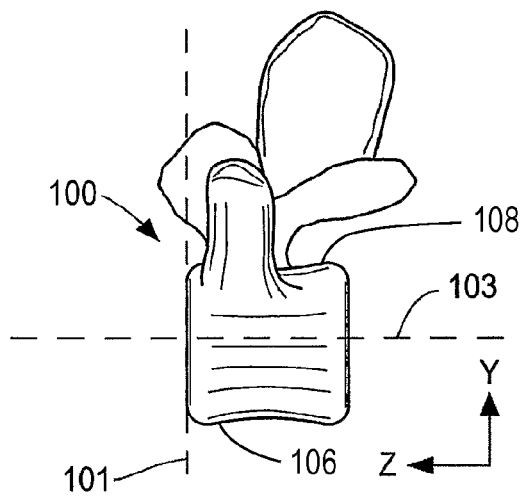
Figure 1B:
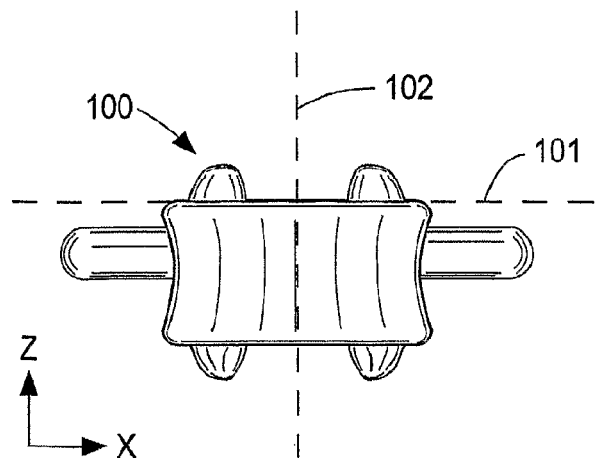

FIGS. 1A, 1B, and 1C illustrate superior (or plan), anterior, and lateral views, respectively, of a representative vertebra 100. The figures illustrate orthogonal planes with reference to the vertebral body endplate, which, of course, correspond to planes of the corresponding intervertebral prosthesis endplate. The XY plane 101 lies generally parallel to the vertebral body endplate and may be described as a transverse plane. The YZ plane 102 is a medial plane extending in an antero-posterior direction and parallel to a sagittal plane of the vertebral body. The XZ plane 103, perpendicular to both XY and YZ planes, lies approximately at the midpoint of the antero-posterior dimension of the vertebral endplate and extends laterally, cranially, and caudally, and thus may be described as a coronal plane. The skilled practitioner will understand that the anatomical directions indicated above, as well as in the following description, are to be taken with respect to the vertebral endplate and the corresponding intervertebral prosthesis endplate, and that such directions referenced to the vertebra itself may not correspond exactly to the anatomical directions referenced with respect to the body of a patient, due to the curvature of the spine with concomitant angular positioning of the vertebra and implanted prosthesis.

Figure 2:
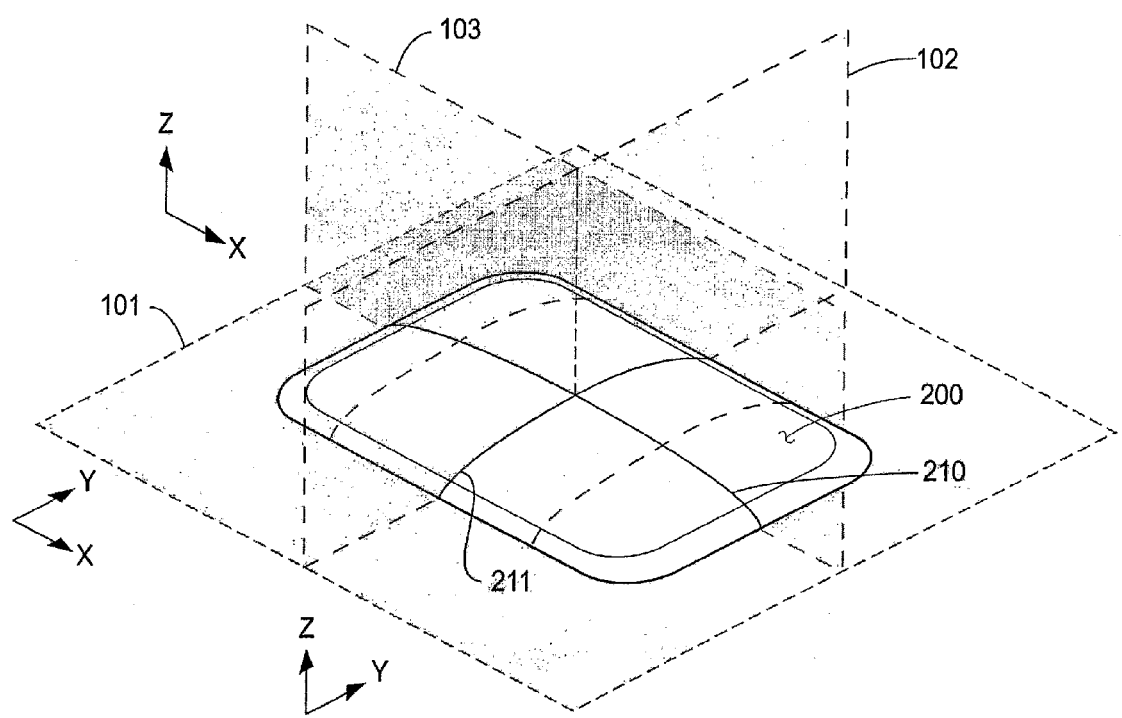
FIG. 2 illustrates a three-dimensional envelope that defines the dome surface of the prosthesis endplate of the invention.

FIG. 2 illustrates a three-dimensional envelope defining the shape of the central domed region of the prosthesis of the invention as well as the corresponding shape of the recess to be generated in the vertebral endplate. Orthogonal transverse plane XY coincides generally with the vertebral body endplate as defined in FIG. 1. Similarly, orthogonal median plane YZ is the midline vertical plane, and XZ, a coronal plane, is perpendicular to both XY and YZ planes.

The envelope defining the surface 200 of the dome is defined by the antero-posterior profile 211 and the transverse profile 210. The surface of the dome is typically generated using the instruments of this invention by moving a shaped cutter in a defined trajectory against a vertebral endplate. Thus, for example, the antero-posterior profile 211, in the YZ plane, may be formed by a corresponding antero-posterior profile of a cutting instrument moved along a transverse trajectory indicated by the profile 210, in the XZ plane, to form the resultant domed surface. Accordingly, in the following discussion, the dome shapes of the various embodiments of the prosthesis endplate of the invention may be described in terms of the profiles and trajectories of the cutting tools.

Figure 3A:
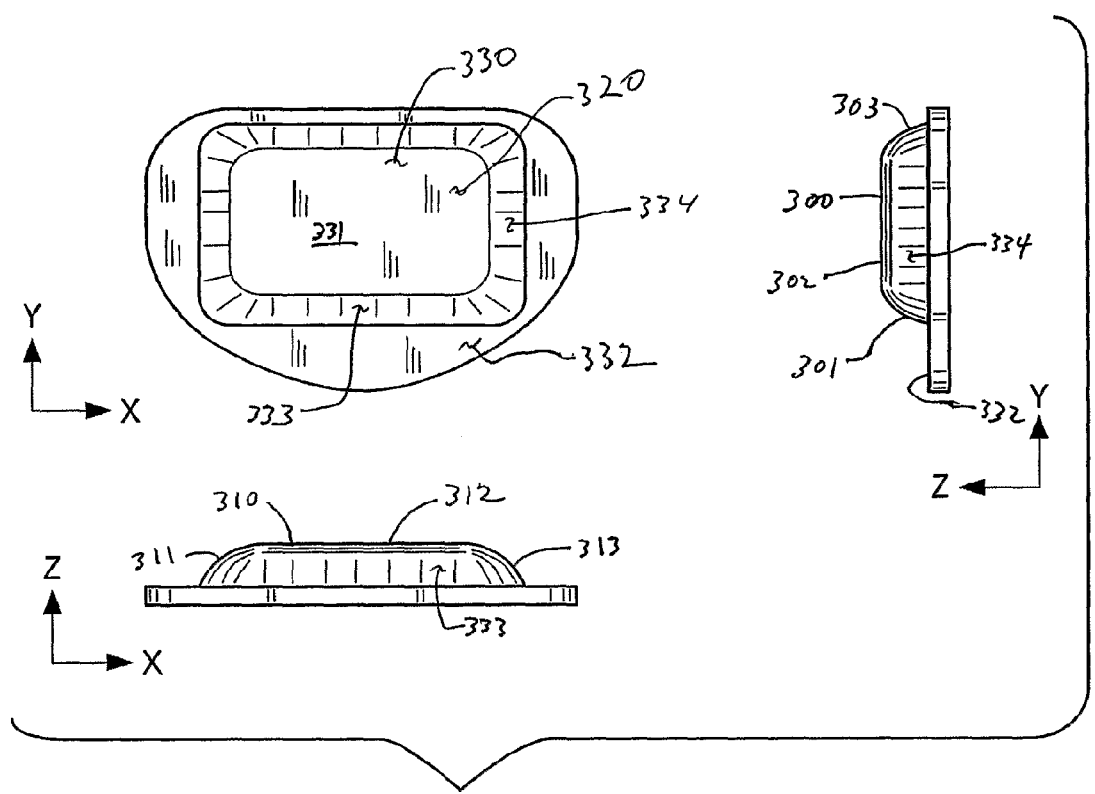
FIG. 3A illustrates three orthogonal views of one embodiment of this invention.

FIG. 3A illustrates three orthogonal views, i.e., plan, anterior elevation and lateral elevation, of an embodiment of this invention with dome 330 having a surface defined by antero-posterior profile 300 and transverse profile 310. Such a surface may typically be constructed by moving a milling cutter having a complementary antero-posterior profile 300 in a transverse trajectory indicated by profile 310. Antero-posterior profile 300 and transverse profile (or trajectory) 310 are formed by three geometric segments. As illustrated in FIG. 3A profile 300 comprises an arc 301, a line 302 and an arc 303. Similarly profile (or trajectory) 310 comprises an arc 311, a line 312 and an arc 313. Surface 320 is the resulting surface when profile 300 is protruded along trajectory 310. In this embodiment, a flat region 332 of the rim is maintained with the dome surface covering only a portion of the implant plan area. Rim region 332 is aligned with the vertebral body endplate, generally in contact with the dense bone rim of the vertebra, providing alignment and additional subsidence resistance.

Advantageously the surface 320 of dome 330 intersects flat surface 332 at an obtuse angle resulting in dome surface regions 333 and 334 providing for high resistance to extrusion and high resistance to relative torsional motion if the prosthesis endplate with respect to the vertebra body. Top flat region 331 of the dome 330 region allows for minimal bone removal from vertebral body endplates as well as intervertebral space and minimizes the amount of distraction required for insertion of the intervertebral prosthesis.

Figure 3B:
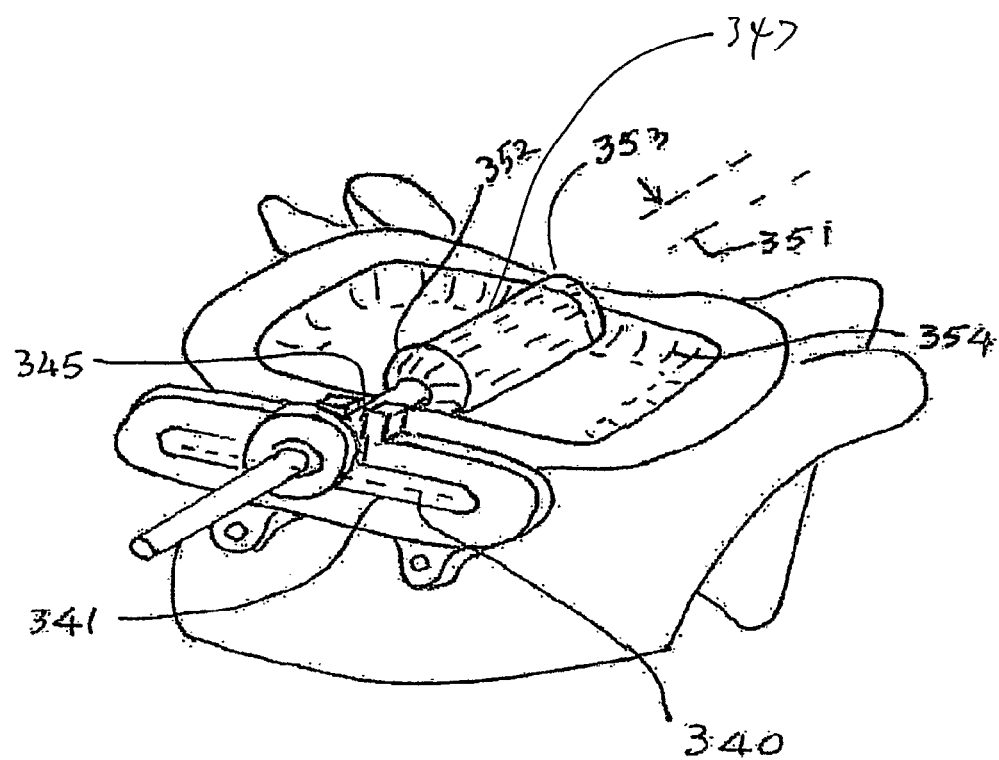
FIG. 3B is a partial perspective and cut away view of a cutter and guide, of the type illustrated generally in FIGS. 11, 16, and 20, for preparing a recess in a vertebral endplate for receiving a prosthesis endplate as illustrated in FIG. 3A.
Figure 3C:
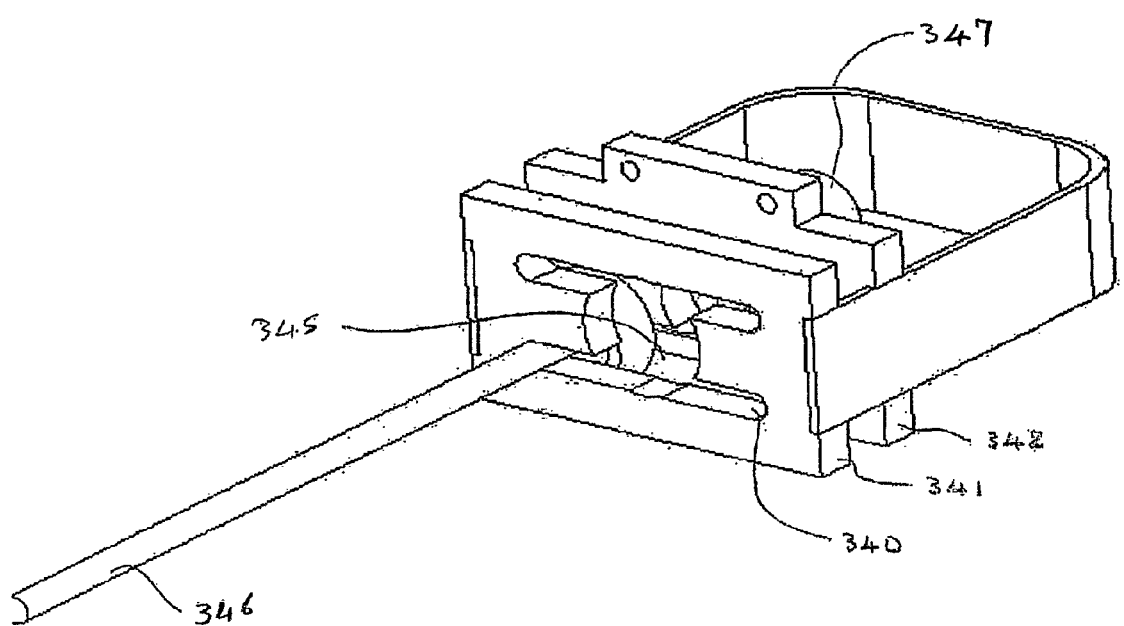
FIG. 3C is a more complete perspective view, generally equivalent to FIG. 20.
Figure 3D:
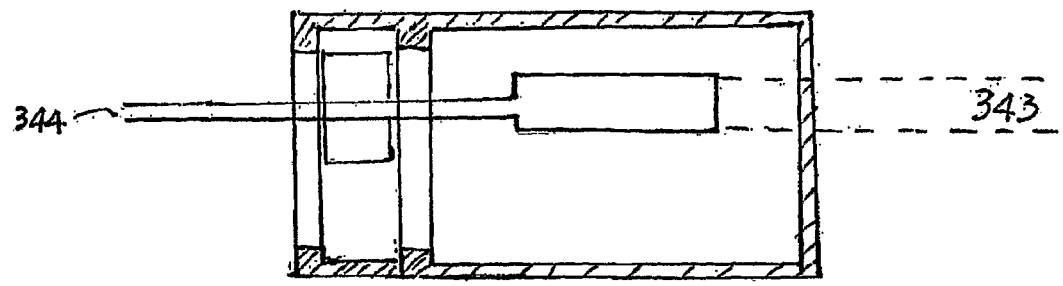
FIG. 3D is a diagrammatic top view and FIG. 3E is a side partial sectional view of the forming tool and guide of FIG. 3B.
Figure 3E:
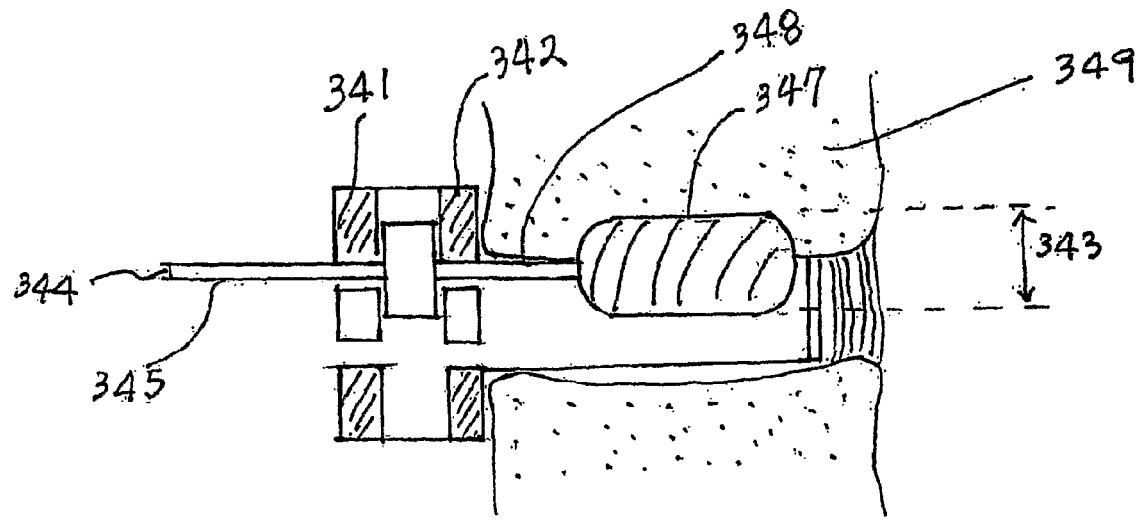
Figure 16:
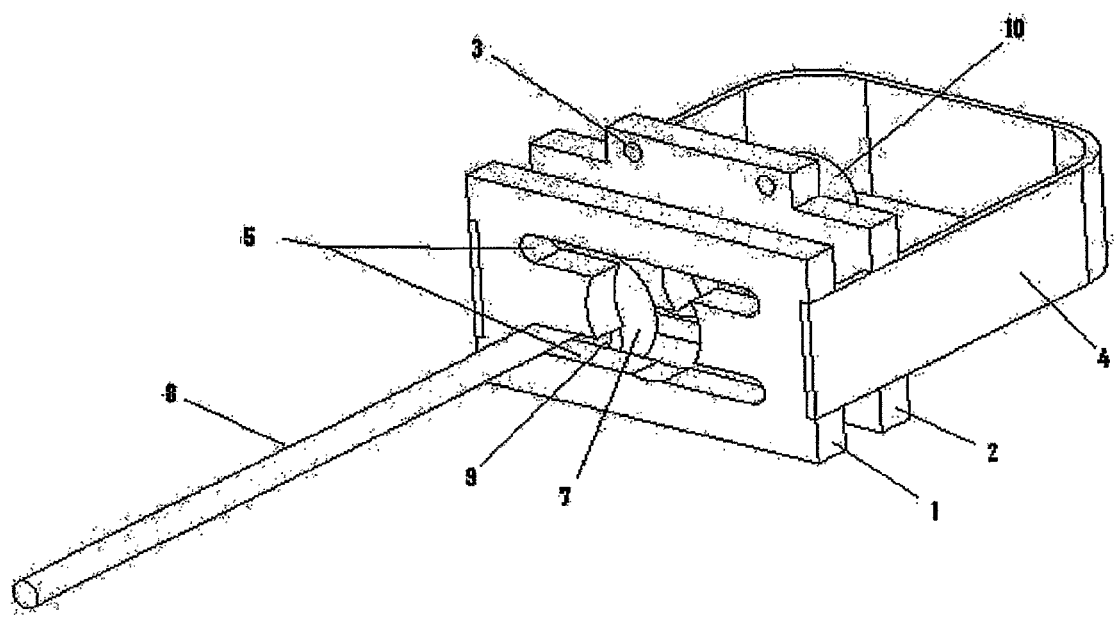
FIG. 16 is an oblique view of an embodiment of the invention wherein the cutting tool has been inserted into the guide frame, showing the cutting tool moved to a lateral extremity of the lower guide slot.

FIG. 3c is a perspective view, generally equivalent to FIG. 16 (described in more detail below), with the reference numerals keyed to the procedure illustrated in FIG. 3E, of an embodiment of the instruments used for preparing the domed prosthesis endplate of the invention. FIG. 3D is a diagrammatic top view, of the instrument. FIG. 3E is a side elevational partial sectional view of the forming tool in use, with the vertebral body outlined to better illustrate the function and features of the present invention. The forming tool 347 is shown inserted into the tool guide of FIG. 16A, with drive shaft 346, having a diameter 344, extending through guide channel 340 in anterior plate 341 and a corresponding guide channel in posterior plate 342, each of the plates being provided with straight guide channels and openings to form an insertion channel 345. Advantageously, the insertion channel is positioned such that the cutting tool 347 may be inserted into the intervertebral cavity without interference with the vertebral body endplates or peripheral rim of the vertebra. Channel 345 is connected, e.g., to guide channel 340 such that, after insertion, forming tool 347 can be advanced in the direction of the endplate and along a path defined by guide channel 340 to form the dome recess, without removing bone from any other part of the vertebral endplate including the peripheral rim. As illustrated, the tool diameter 343 is larger than the drive shaft shank diameter 344 which allows for the formation of a dome cavity without damaging the anterior bone rim 348 of the vertebral body 349.

FIG. 3B is a partial perspective view, where part of the guide is removed for clarity, schematically illustrating the forming tool 347 inserted into the guide channel and depicts the shape and diameter of the tool that would generate the corresponding concavity on the vertebral body endplate when it is operated and is made to follow the guide channel 340. The tool radius 351 is equal to arcs 311 and 313 and the tool fillet radii 352 and 353 are equal to profile arcs 301 and 303 of profile 300. Thus, when the tool is inserted into the guide channel and moved along a straight line path defined by guide channel 340 with the cutting surface of the forming tool moving at a distance from a transverse plane generally defining the middle of the intervertebral space along the spinal axis, shown by line 312 of the profile (or trajectory), the concavity formed will have an accurate fit to the implant rim surface 332 and dome surface 320.

Alternate embodiments described below utilize different combinations of cutter profile and guide channel shapes resulting in various tool trajectories and corresponding dome profiles. These alternate embodiments allow the optimization of features that are typically matched to the desired performance of the implant based on its size, position, stiffness and motion characteristics.

Figure 4A:
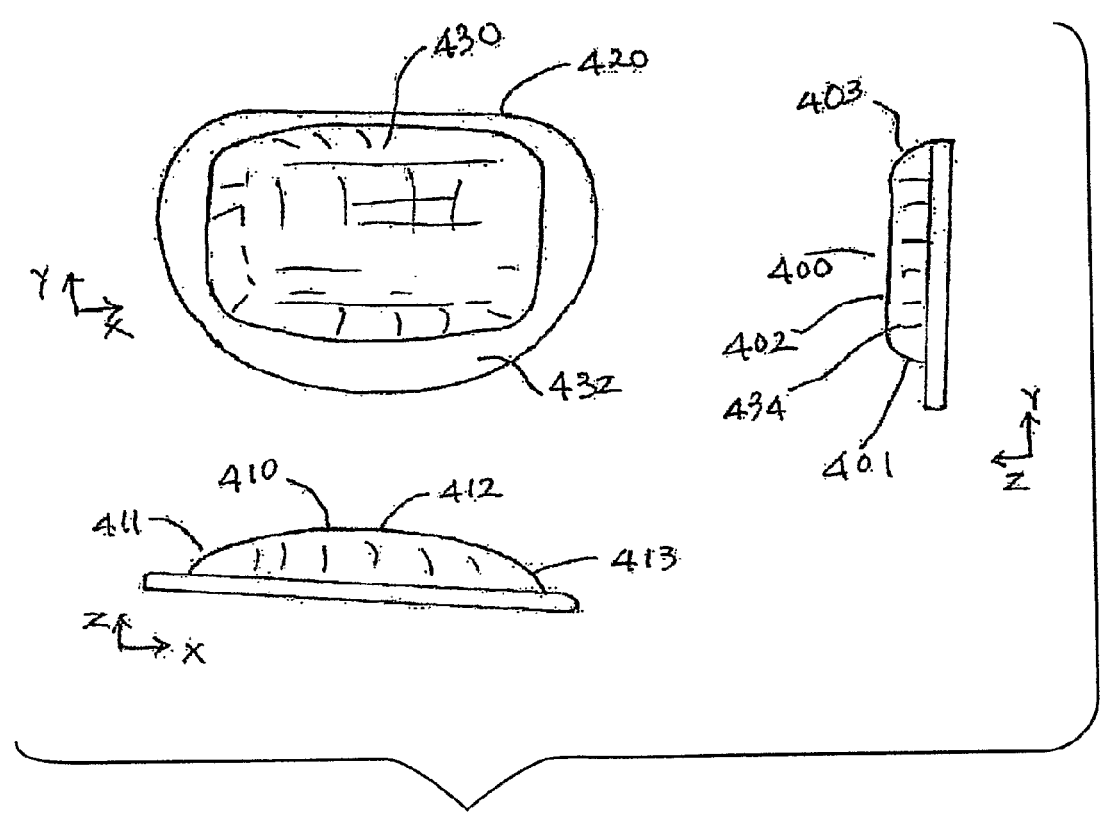
FIG. 4A illustrates an alternate embodiment of the invention showing a domed surface of somewhat different shape from that of FIG. 3A.
Figure 4B:
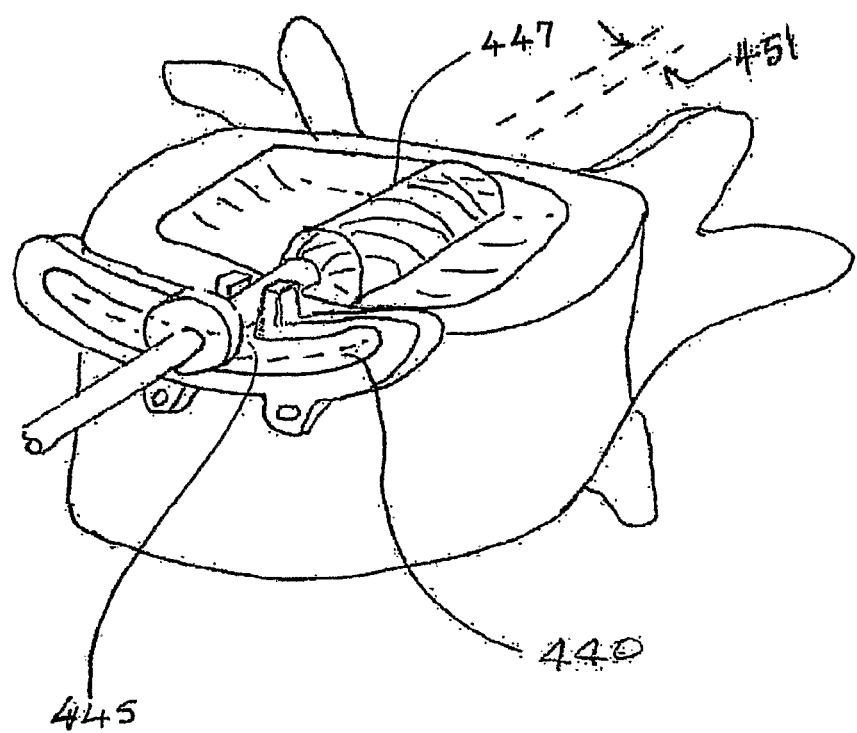
FIG. 4B is a partial perspective and cut away view of a cutter and guide similar to FIG. 3B, but for preparing a recess in a vertebral endplate for a prosthesis endplate of FIG. 4A.

FIGS. 4A and 4B illustrate an alternate embodiment of the invention wherein the antero-posterior profile 400 is identical to 300 and the transverse profile (or trajectory) 410 is comprised of a first arc section 411, a second arc section 412, and a third arc section 413. As in the configuration illustrated in FIG. 3A, the antero-posterior profile and transverse profile are confined to an inner region of the implant plan periphery, resulting in a raised dome section 420 and a planar section 421. In this embodiment, as in the other embodiments of the invention, when a prosthesis incorporating an endplate according to this invention is implanted, the planar rim, 421 in this embodiment, is positioned generally parallel to the vertebral body endplate providing additional rotational stability about an axis of rotation in the XY plane. Profile 410 contains arc 412, formed by an arcuate guide channel 440 as shown in FIG. 4B. FIG. 4B, similar to FIG. 3B, is a partial perspective view, where part of the guide is cut away for clarity, illustrating the forming tool 447 inserted into the guide channel and depicts the shape and diameter of the tool that would generate the corresponding concavity on the vertebral body endplate when it is operated and is made to follow the arc channel 440. The centerline path of the guide channel is arc 440 having a radius equal to the radius of arc 412 FIG. 4A minus the radius 451 of tool 447. Thus, when the tool is inserted into the guide channel it follows a path defined by arc 440, and the concavity formed will have an accurate fit to the implant surfaces 432 and dome 430. Channel 445 is connected to guide channel 440 such that, after insertion, forming tool 447 can be advanced in the direction of the endplate and along path 440 to form the dome recess without removing bone from any other part of the vertebral endplate including the peripheral rim.

Figure 5A:
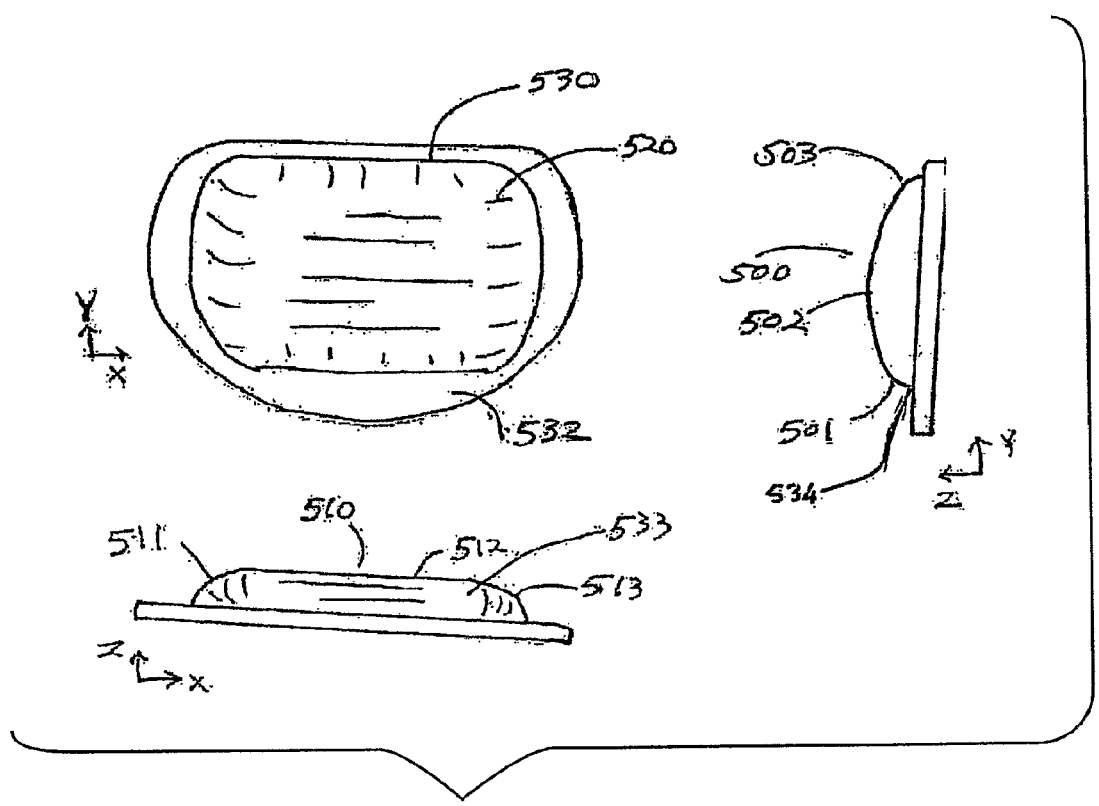
FIG. 5A illustrates a further embodiment of the prosthesis endplate of the invention.
Figure 6A:
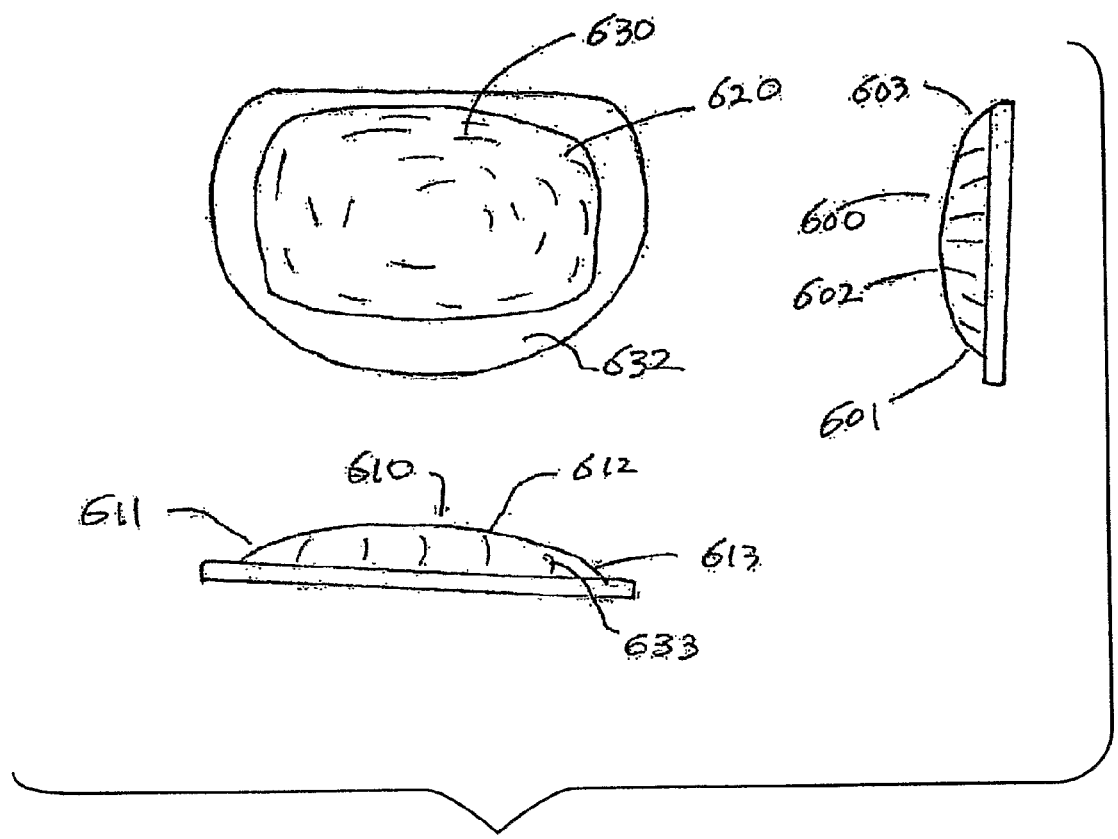
FIG. 6A illustrates a further embodiment of the prosthesis endplate of the invention.

Additional alternate embodiments are illustrated in FIGS. 5A and 6A. In these alternate embodiments the dome is constructed by combinations of alternate antero-posterior profiles and transverse profiles (or trajectories) comprising lines, circular and elliptical arcs and splines adapted to particular applications.

FIG. 5A is an illustrative example where the antero-posterior profile is constructed by an arc 502, a second arc 503, and a third arc 504, and the transverse profile (or trajectory) trajectory 510 is similar to trajectory 310 of FIG. 3A, where curve 510 is constructed by a first arc section 511, a second line section 512, and a third arc section 513. Advantageously arc 502 and arc 504 intersect flat section 532 at an obtuse angle.

In a series of experimental tests, the resistance to shear loading of these domes was compared to simple flat surfaces as well as the embodiments wherein either fins or spikes were added to the domes. In these tests, blocks of polyurethane foam corresponding in hardness and strength to human cancellous bone were used as a reproducible and consistent surrogate. (Pacific Research Laboratories, Vashon, Wash.: Type 1522-01 with a compressive strength of 2.2 MPa and a shear strength of 1.4 MPa). Discs having both superior and inferior surfaces of different shapes and adjunct fixation were tested in shear. Failure in all cases occurred within the bone substitute material. The results are summarized in Table 1 below and indicate the superiority of a dome shape surface as illustrated in FIG. 5A:

TABLE 1

|  | Flat Surface (i.e No Dome) | Dome Alone | Dome with Anterior Spikes & No fin | Dome with Anterior Spike & Fin |
|---|---|---|---|---|
| Mean | 158N | 398N | 388N | 368N |
| Std Dev | ±9N | ±389N | ±76N | ±33N |

Figure 5B:
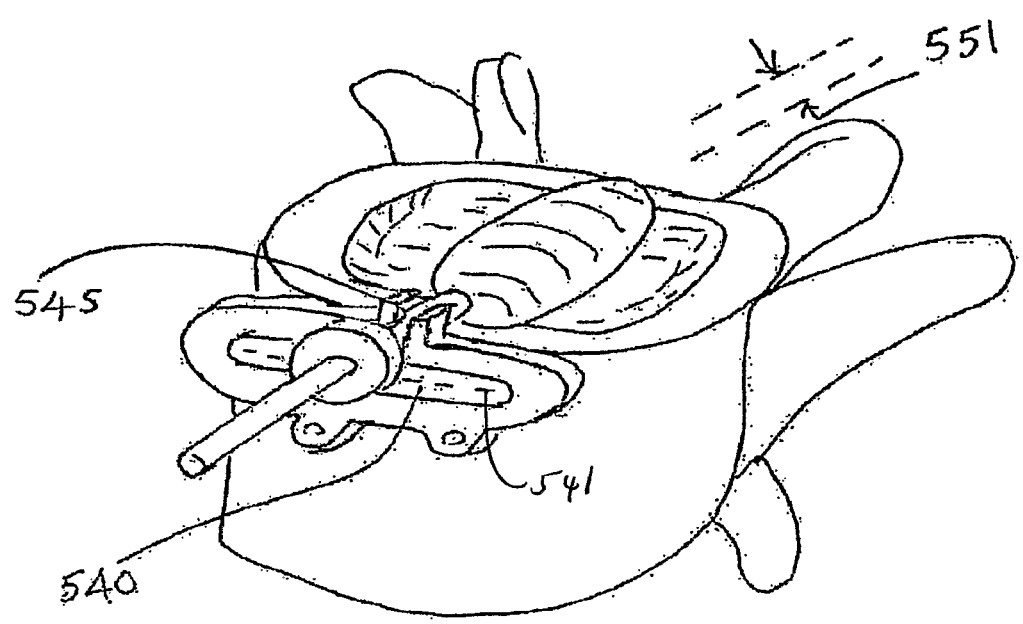
FIG. 5b is a partial perspective and cut away view of a cutter and guide similar to FIG. 3B, but for preparing a recess in a vertebral endplate for a prosthesis endplate of FIG. 5A.

Test Conditions: 2.5 mm per minute crosshead speed.
225N compression across disc FIG. 5B is a partial perspective view, where part of the guide is removed for clarity, illustrating the forming tool inserted into the guide channel and depicting the shape and diameter of the tool that would generate the corresponding concavity in the vertebral body endplate when it is operated and is made to follow channel 540 having a linear form similar to the guide of FIG. 3B. The centerline path of the guide channel is line 541 having a length equal to line section 512. Thus, when the tool is inserted into the guide channel and moved along a path defined by line 541, the concavity formed will have an accurate fit to the implant surfaces 532 and dome 530. Channel 545 is connected to guide channel 540 such that, after insertion, forming tool 547 can be advanced in the direction of the endplate and along path 540 to form the dome recess without removing bone from any other part of the vertebral endplate including the peripheral rim.

FIG. 6A is an illustrative example where the antero-posterior profile 600 is constructed by an arc 602 a second arc 603 and third arc 603 and the transverse profile (or trajectory) 610 is similar to trajectory 410 of FIG. 4A where curve 610 is constructed by a first arc section 611 and a second line section 612 and a third arc section 613.

Figure 6B:
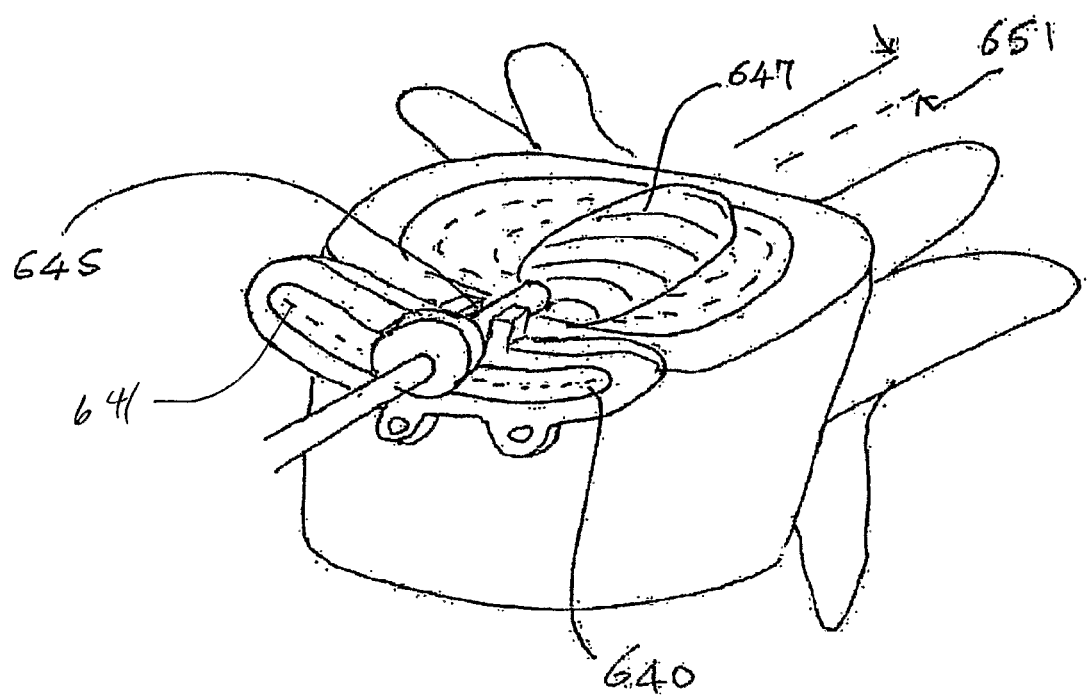
FIG. 6B is a partial perspective and cut away view of a cutter and guide similar to FIG. 3B, but for preparing a recess in a vertebral endplate for a prosthesis endplate of FIG. 6A.

FIG. 6B is a partial perspective view, where part of the guide is removed for clarity, representing the forming tool inserted into the guide channel and depicting the shape and diameter of the tool that would generate the corresponding concavity on the vertebral body endplate when it is operated and is made to follow the guide channel 640. Again, with forming tool 650 and the guide 640 having an arc guide channel similar to the guide of FIG. 4B, the centerline path of the guide channel is line 641, having a length equal to line section 612. Thus, when the tool is inserted into the guide channel and it follows a path defined by line 641, the concavity formed will have a line-to-line fit to the implant surfaces 632 and dome 630. Channel 645 is connected to guide channel 640 such that, after insertion, forming tool 647 can be advanced in the direction of the endplate and along path 640 to form the dome recess, without removing bone from any other part of the vertebral endplate including the peripheral rim.

FIG. 7A is an illustrative example wherein the domed surface 709 has an antero-posterior profile 708 constructed by a single arc 712 and the transverse profile trajectory 710 is also constructed by a single arc 711. In this embodiment the defining section and trajectory arcs run-out of the implant plan profile result in the elimination of the flat regions disclosed in the alternate embodiments above. In addition, the absence of specific margins on the resultant full bi-curvature convex dome reduces its anti-rotational characteristics, but allows for minimal endplate removal thus enhancing the overall bone to implant interface strength.

Figure 7B:
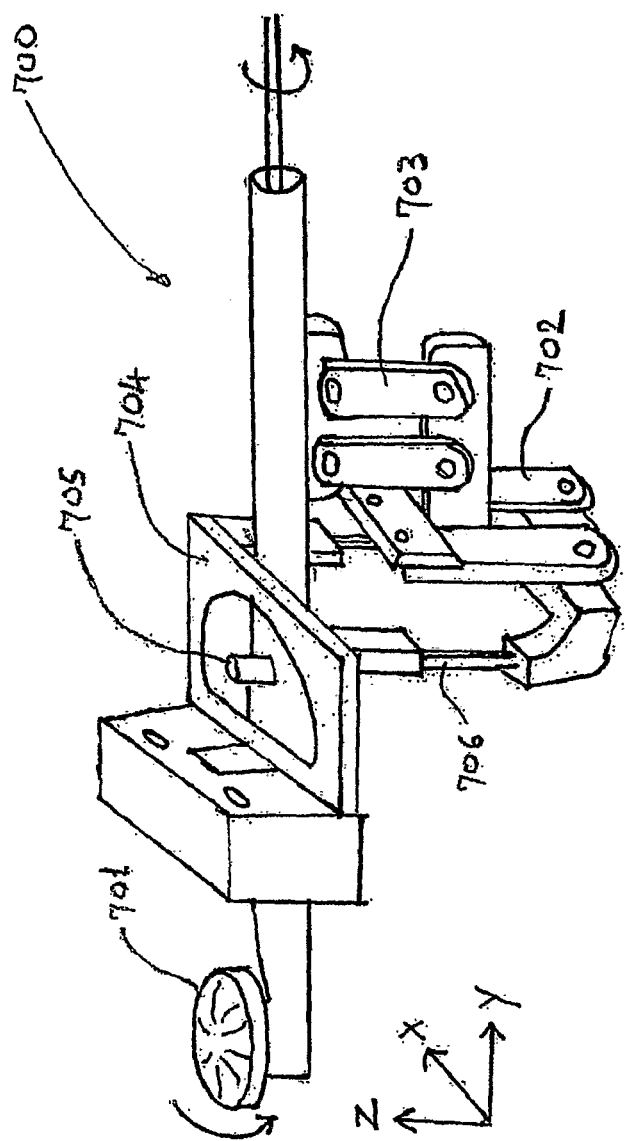
FIG. 7B is a perspective view of a cutter and guide for forming a recess in a vertebral endplate for receiving a prosthesis endplate of FIG. 7A.

FIG. 7B is an illustrative example of the forming tool utilized to form the bi-curvature dome illustrated in FIG. 7B. The surgical cutting tool of FIG. 7B is described in detail in copending application by one of the inventors, application Ser. No. 11/340,505, filed on Jan. 27, 2006, the entire disclosure of which is incorporated herein by reference. The structure and use of such a cutter is summarized in the following. The use of a forming method utilizing a guide as described above will require the tool to travel a path having an XY plane length equal to the implant lateral width. With the forming tool having such a path the cutting portion of the tool will over-cut part of the remaining annulus. In the embodiment of FIG. 7B the forming tool 701 is guided by a set of linkages that control its travel in the section curve and the trajectory curve directions. The cutting face of the tool is rotated about an axis perpendicular to the XY plane and the resultant combination of trajectory linkages, section linkages and tool diameter will form the bi-curvature recess that matches the implant dome illustrated in FIG. 7B. Slider 706 permits the introduction of the forming tool through the intervertebral anterior opening and the subsequent formation of the dome cavity recess posterior to the vertebral body bony rim. The shape of this template defines the plan shape of the implant endplate such that the dome recess is limited to the implant size and form. This also allows for the full plan shape to be countersunk into the vertebral endplate without excess bone removal. Countersinking will enhance the torsional stability of the implant. Guide 700 is attached to the vertebral body and referenced to the vertebral endplate plane. A low profile right angle drive cutting tool 701 having a partial spherical shape is attached to four bar linkage mechanism 703 that controls the tool's path in the YZ plane. The ground link of mechanism 703 is attached to the connecting rod of four bar linkage mechanism 702 which now controls the tool's path in the XZ plane. The ground link of mechanism 702 is attached to slider 706 which guides the tool position in the Z direction allowing the tool to be inserted within the intervertebral space and advanced in the Z axis direction towards the vertebral endplate to perform the dome forming operation. Template 704 fixed to the vertebral body attachment of guide 700 and pin fixed to tool 701 define the extent of travel of the cutting tool in the YX direction. The shape of template 704 defines the plan shape of the implant endplate such that the dome recess is limited to the implant size and form. This also allows for the full plan shape to be countersunk into the vertebral endplate without excess bone removal.

Figure 8A:
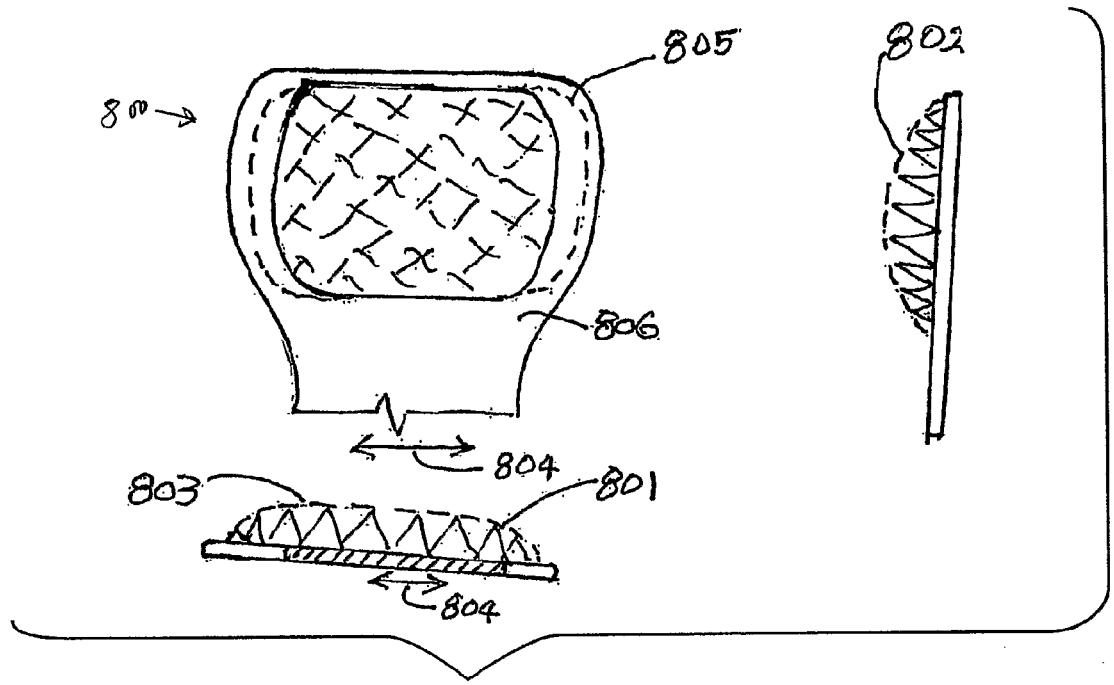
FIG. 8A illustrates an alternate forming tool for forming a recess in a vertebral endplate for receiving a prosthesis endplate according to the invention.
Figure 8B:
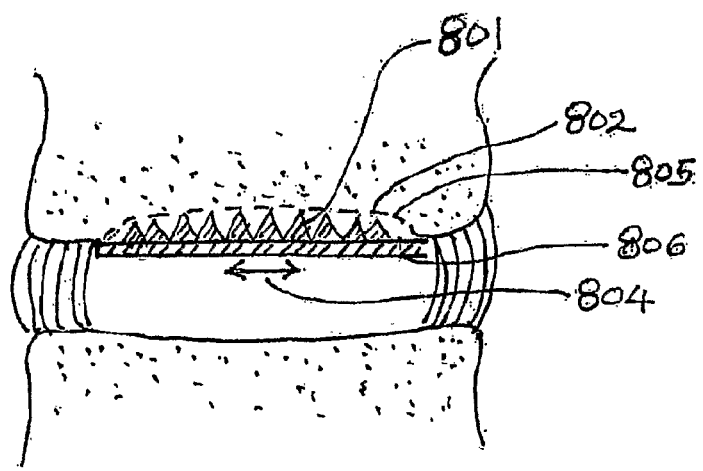
FIG. 8B is a partial anterior sectional view of tool 800 in position within an intervertebral space for forming a recess to receive the dome of a prosthesis endplate according to the invention.

FIG. 8A illustrates an alternate forming tool and forming method, wherein the forming tool 800 utilizes translational motion of a formed rasp to generate the dome recess on the vertebral endplate. Tool 800 has bone cutting teeth 801 having the outline form of profile 802 and a truncated path 803 as illustrated in FIG. 8A. Translation of rasp 800 in a direction parallel to path 804 by a distance equal to the path truncation as compared to the corresponding dome profile will form a concavity on the vertebral body endplate having the corresponding implant dome form indicated by outline 805. When tool 800 is positioned within the intervertebral space and the rasping operation is performed, flat region 806 will restrain the rasp from cutting a concavity deeper than the dome height defined by trajectory 802 or path 803, thus maintaining the peripheral margin of the vertebral body FIG. 8B is a partial lateral sectional view of tool 800 positioned at its final position when forming the dome recess on the superior vertebral body endplate. FIG. 2 defines the three dimensional envelope used to generate the dome surface.

Figure 9A:
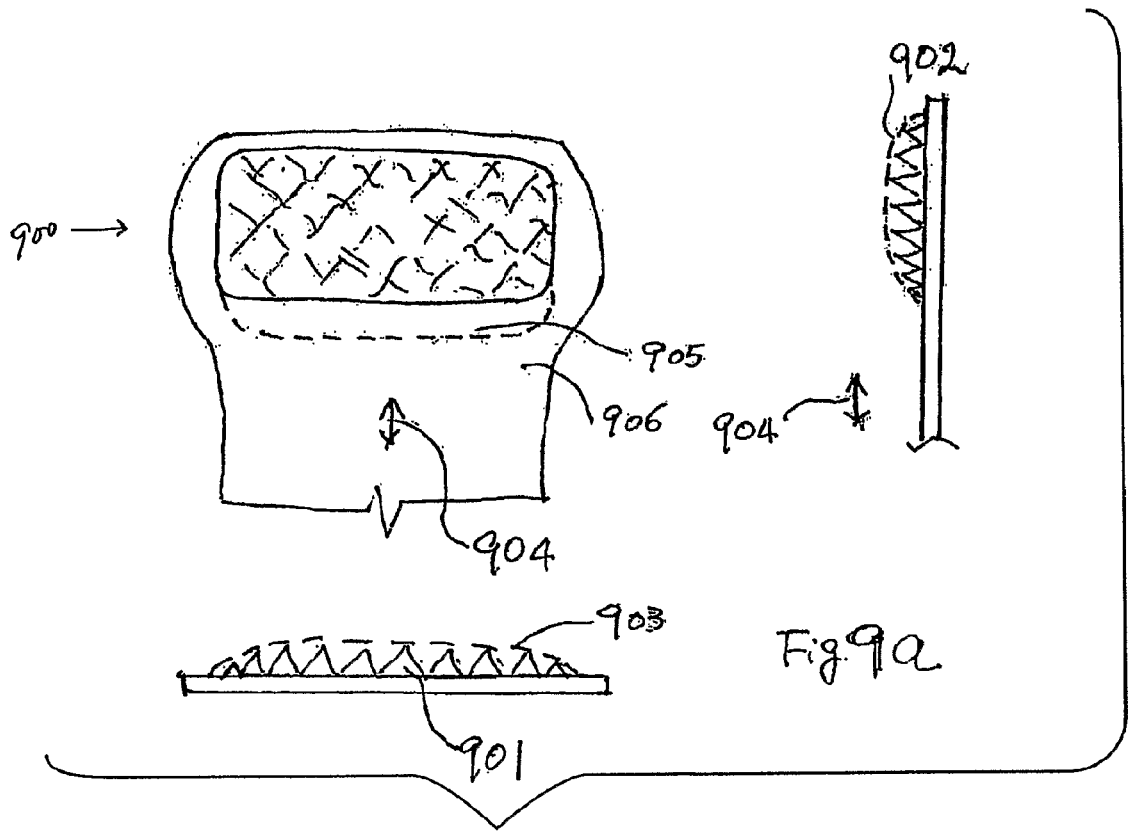
FIG. 9A illustrates a variation of the forming tool of FIG. 8A suitable for forming a recess to receive a prosthesis endplate according to the invention.

FIG. 9A illustrates another forming tool suitable for forming a recess in a vertebral endplate wherein forming tool 900 utilizes translational motion of a formed rasp to generate the dome recess on the vertebral endplate. Tool 900 has bone cutting teeth 801 having the outline form of a truncated trajectory 902 and path 903 as illustrated in FIG. 2. Translation of rasp 900 in a direction parallel to path 904 by a distance equal to the path truncation as compared to the corresponding dome profile, e.g., profile 210 in FIG. 2, will form a concavity on the vertebral body endplate having the corresponding implant dome form indicated by outline 905. When tool 900 is positioned within the intervertebral space and the rasping operation is performed, flat region 906 will restrain the rasp from cutting a concavity deeper than the dome height defined by trajectory 902 or path 903, thus maintaining the peripheral margin of the vertebral body.

Figure 9B:
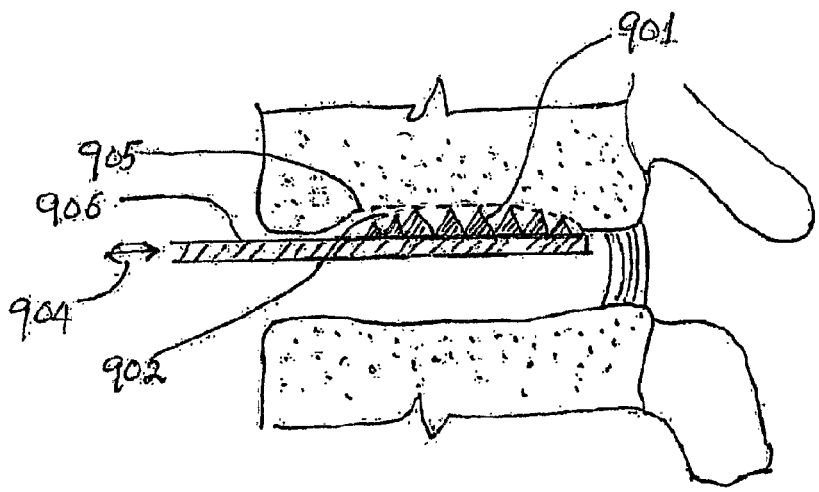
FIG. 9B is a partial lateral sectional view of tool 900 in position within an intervertebral space for forming a recess to receive the dome of a prosthesis endplate according to the invention

FIG. 9B is a partial anterior sectional view of tool 900 inserted into its final position when forming the dome recess on the superior vertebral body endplate.

Figure 10:
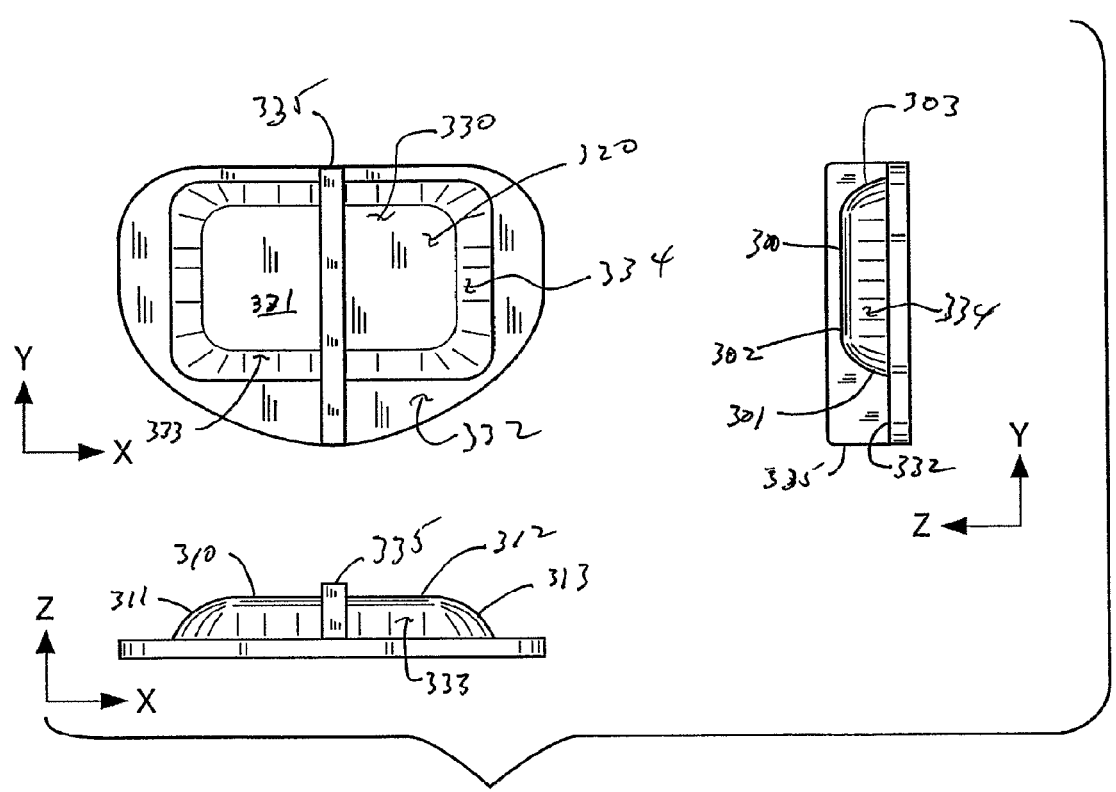
FIG. 10 illustrates a further embodiment of the prosthesis endplate of the invention, similar to that of FIG. 3A, additionally incorporating a fin.

FIG. 10 illustrates a further embodiment of the prosthesis endplate of the invention, similar to that of FIG. 3A, additionally incorporating a fin 335.

Instruments for preparing a recess in a vertebral endplate suitable for receiving a complementary domed region of an intervertebral prosthesis endplate according to the invention will be described with reference to FIGS. 11-29.

A surgical cutting tool for milling a recess in a vertebral endplate to receive a portion, (e.g., a complementary surface) of an intervertebral disk prosthesis according to the invention comprises a guide frame and a surgical cutting tool inserted into the guide frame and guided thereby to mill the recess.

The guide frame is adapted to be attached to at least one of the vertebrae adjacent to the intervertebral space. As indicated in the attached drawings, in a preferred embodiment, the guide frame is adapted to be inserted into the intervertebral space after at least a portion of the intervertebral disc has been removed. It comprises a generally U-shaped guard rail and a pair of guide plates, anterior and posterior, supported by the guard rail. The U-shaped guard rail has a base portion generally corresponding to the bottom of the U-shape and a pair of support arms extending from the ends of the bottom portion. The guide plates are supported on the support arms generally near the distal, i.e., the anterior, ends thereof and are spaced from one another in an anterior-posterior (AP) direction to receive and cooperate with a positioning collar disposed on the drive shaft of the surgical cutting tool, as will be discussed in more detail below. In use, the assembly of guard rail and guide plates is sized to be positioned within a surgically prepared intervertebral space, e.g., after removal of all or a portion of the intervertebral disk and suitable distraction of the adjacent vertebrae, with the base portion of the guard rail positioned at or near the posterior margin 108 the vertebral bodies and the guide plates positioned generally at the anterior margin 106 of the vertebral bodies. Holes are provided in at least one of the guide plates for fastening the assembly to the vertebral bodies with conventional screws, pins, or the like.

The guide plates are provided with generally central apertures through which a surgical cutter, e.g., a milling cutter or burr, can be inserted into the intervertebral space, and with laterally oriented guide channels or slots which guide the motion of the surgical cutter as will be discussed below. The surgical cutter is provided with a drive shaft that extends anteriorly from the cutter and terminates in a distal anterior end at a position typically located anterior to the vertebral column where it can be conveniently attached to any conventional means for driving the surgical cutter, e.g., in rotation. Thus, the cutter can be driven by any conventional motor, e.g., an electric motor, or even by a hand-operated mechanism. A positioning collar is fixed at a location along the drive shaft and cooperates with the guide plates to position the cutter within the intervertebral space to perform the requisite milling or reaming of the endplates of the adjacent vertebrae. To this end, the collar has a diameter somewhat larger than that of the surgical cutter, and the insertion aperture or hole in the anterior guide plate is made large enough for both the cutter and collar to pass through, but the insertion aperture in the posterior guide plate is only large enough to allow the cutter to pass through. Accordingly, when the cutter is fully inserted into the intervertebral space, the positioning collar is located between the anterior and posterior guide plates. This arrangement permits transverse motion guided by the guide slots in the plates, but fixes the cutter in a predetermined position along an anterior-posterior (AP) axis. Guide slots or channels in the guide plates permit the drive shaft with attached cutter to move in a predetermined lateral and vertical pattern, whereby the cutter can remove a precisely determined portion of the vertebral endplates to prepare seats for accepting an intervertebral disk prosthesis.

The skilled practitioner will recognize that in certain circumstances, certain elements of the surgical cutter guide as described may be omitted, without departing from the spirit of the invention. For example, the guard rail may not be required if other means are used to maintain distraction of the vertebrae to permit operation of the surgical cutter. Similarly, depending on the circumstances of the surgical site and/or the preferences of the surgeon, only a single guide plate may be used, provided with one or two guide slots as desired for milling the endplates of one or both of the adjacent vertebrae, or the guide collar on the drive shaft of the surgical cutter may be omitted. Likewise, in some circumstances, it may be appropriate to attach the guide plate, or the guide frame, to only one of the adjacent vertebrae.

The surgical cutting tool guide of the invention is intended to be used in a surgical procedure for replacing a degenerated intervertebral disc with an intervertebral disc prosthesis. In using the cutting tool guide, the spinal column is exposed through an anterior approach, and the disc and adjoining vertebral bodies are adequately exposed. Following the adequate removal of the annulus and nucleus, the disc space is distracted.

Thereupon, the endplate forming guide is positioned to guide the surgical cutting tool. In using the illustrated embodiment, the guardrail is positioned within the intervertebral space, and the guide frame is preferably attached to the adjoining vertebral bodies above and below the disc space with screws or pins inserted through at least one of the guide plates. A cutting tool having a predetermined size and shape is then inserted into the endplate forming guide and the vertebral endplates are milled to the desired geometry.

Preferred embodiments of the surgical cutting tool guide of the invention, are designed to guide the milling of the endplates of vertebrae in preparation for receiving the corresponding structures of the intervertebral disc prosthesis. Preferred embodiments of surgical cutting tools for use with the tool guide are also illustrated in the drawings.

Figure 11:
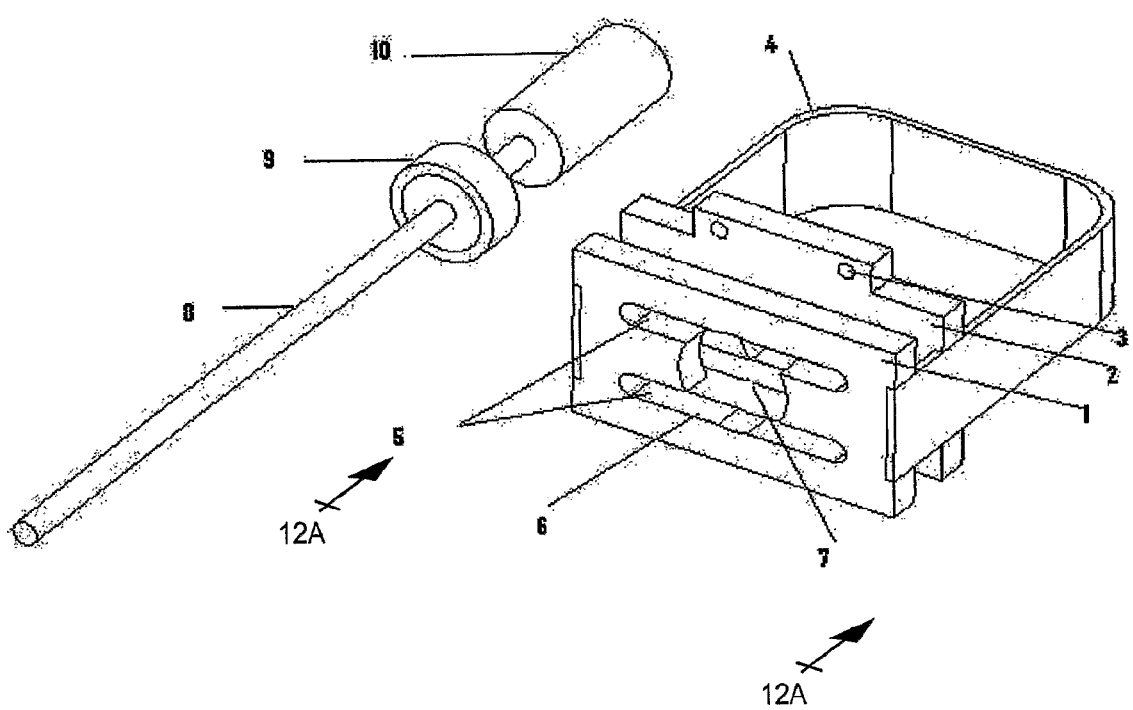
FIG. 11 is an oblique view of an embodiment of the guide frame of the invention together with an embodiment of a surgical cutting tool used therewith.

The illustrated embodiment of the tool guide or frame comprises the following elements:

A. An anterior guide plate (1) (FIGS. 11, 12B) having a generally central aperture or insertion opening (7) for insertion of a surgical cutting tool and guide channel openings or slots (5) that define the desired trajectory of the forming tool. Straight parallel channels are shown in FIG. 11. However, the trajectory of the cutting tool may follow any straight or curvilinear path. Generally the desired path is symmetrical about the midline and the horizontal plane, and the guide channel slots (5) are connected to, and positioned above and below the insertion aperture (7). The size of the insertion aperture (7) is generally larger than that of the cutting or forming tool and the guide collar, thereby permitting insertion of the forming tool (10) and guide collar (9) through the anterior plate. In an alternate embodiment of the invention, the tool guide and cutter may be pre-assembled, so that the surgeon need not insert the cutting tool assembly into the guide frame during the surgical procedure. In such an embodiment the generally central apertures in the anterior guide plate (1) and posterior guide plate (2) need not be large enough to permit passage of the cutting tool (10), but may be merely large enough to permit the passage of the drive shaft (8) of the cutter or forming tool during assembly. Accordingly, in such an embodiment, the generally central apertures in the anterior guide plate (1) and posterior guide plate (2) may be simply slots extending in a generally vertical, i.e., cranial-caudal, direction connecting the guide slots or channels 5 and 5a, respectively.

B. A posterior guide plate (2) (FIG. 12C) having a generally central aperture or insertion opening (7a) for insertion of the surgical cutting tool and guide channel openings or slots (5a) complementary to the guide channels in the anterior guide plate that have generally the same shape and orientation as the guide channel openings in the anterior plate (i.e., parallel in the embodiment illustrated in FIG. 11) and cooperate with the guide channels in the anterior guide plate to define the desired trajectory of the forming tool. In the illustrated embodiment, the size of the insertion opening in the posterior guide plate is larger than that of the forming tool (10) but smaller than that of the guide collar (9). This arrangement permits insertion of the forming tool (10) though the posterior plate, but the guide collar (9) then limits the insertion depth to a value predetermined by the position of the guide collar along the drive shaft. In the alternate option of a pre-assembled guide the generally central aperture in the posterior plate may be sized to permit passage of the drive shaft (8) as indicated above for the anterior guide plate (1).

C. The anterior and posterior guide plates form parallel walls bounding a space therebetween (FIGS. 11 14, 15A, 15B). The guide plates are mounted on the guardrail (4) parallel and in registry to hold the guide channels in alignment. The distance between the guide plates is such that the guide collar fits snugly, but slidably, between them. Consequently, the parallel guide plates capture the collar, thereby accurately positioning and maintaining the cutter at a predetermined insertion depth, and also assuring that the axis of the drive shaft and attached cutter remain perpendicular to the guide plates. The insertion apertures in the illustrated embodiment permit the cutting tool to be inserted after the guide frame has been positioned in the prepared intervertebral space, and also connect the guide channels to permit moving the drive shaft of the cutting tool between the guide channels.

D. Holes (3, 3a) at the superior and inferior margins of the cutting tool guide, e.g., in the posterior guide plate (2), as shown, provide for auxiliary fixation to the vertebral body with pins or screws.

E. The guard rail (4) has a height sized to maintain the vertebral bodies at the required distracted position for the forming operation when it is placed securely into the disc space. The guardrail may have variable shape, height, anterior-posterior dimension, transverse dimension, and angular orientation of the rail or portions thereof with respect to the guide plates and/or adjacent anatomical structures, e.g., the vertebral endplates. Such parameters can be determined according to the needs of the individual patient, the size and shape of the particular surgical cutter used and/or the shape and size of the implant intended to be used. Additionally, the guardrail (4), in the illustrated embodiment, provides circumferential protection, defining a protective zone around the cutter.

The illustrated embodiment of the cutter or forming tool has the following components (see, e.g., FIGS. 11 and 22A):
A. A drive shaft (8),
B. A guide collar (9), fixed in position on the shaft, that defines the desired assembled operating position of the forming cutter. The collar preferably contains a bearing element that allows the shaft to rotate independently of the collar, thereby eliminating the binding and frictional effects of a rotating collar captured between the guide plates.
C. A forming cutter or tool (10), having an appropriate form and size for milling the desired recess on each of the vertebral endplates.

The relative positions of the rail edge, in contact with the vertebral endplates, and of the forming tool, as constrained in position by the guide channels, define the depth of the recess formed, i.e., milled or cut, in the endplate.

Figure 15A:
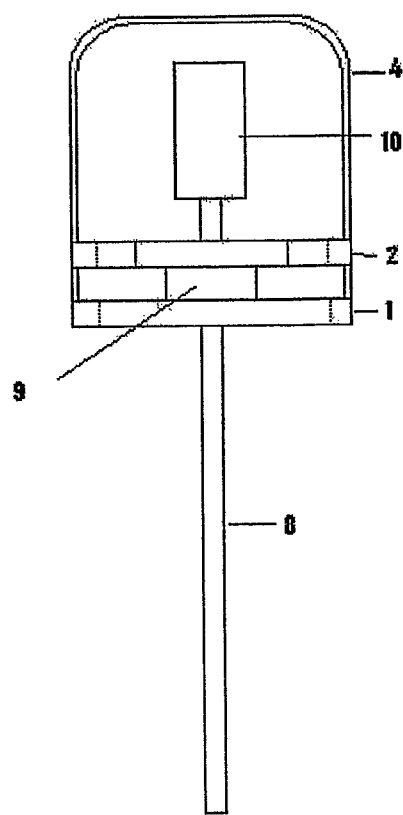
FIG. 15A is a plan view of the assembled guide frame and cutting tool of FIG. 13 wherein the surgical cutter is a cylindrical milling cutter having flat ends.
Figure 23:
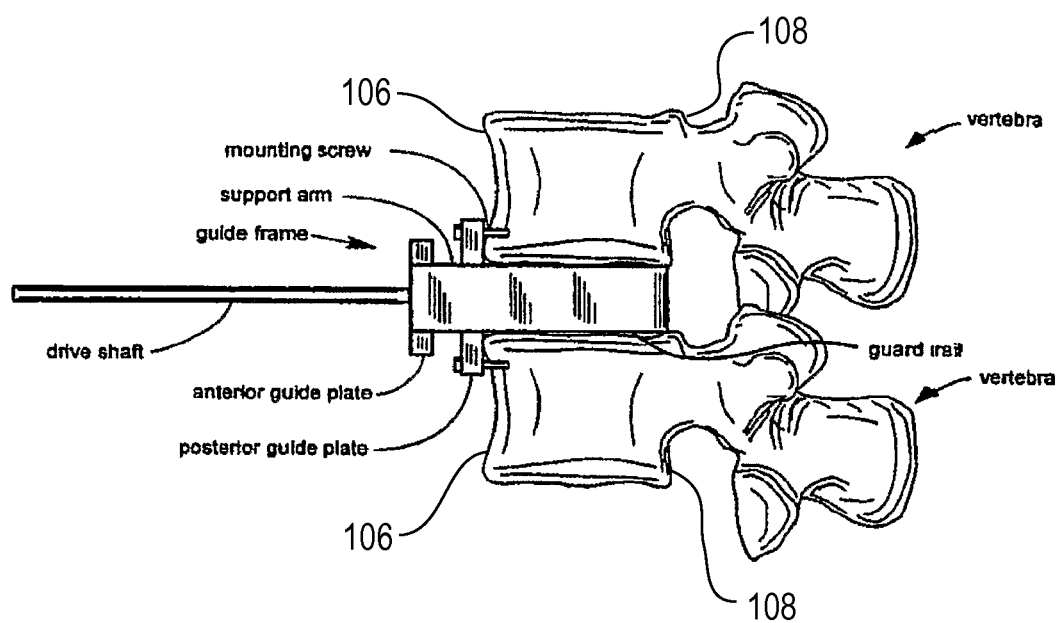
FIG. 23 illustrates the embodiment of FIG. 11 in position between adjacent vertebrae of a spinal motion segment.

Operation of the Tool Guide and Cutter:

The illustrated embodiment of the cutter guide is a two-unit system that is typically assembled and operated by the following procedure.
a) Initially, the surgical tool guide frame is inserted into the prepared disc space, as shown in FIG. 23, and is preferably secured to the vertebral bodies with pins or screws through the provided holes.
b) The forming tool is then inserted through the insertion openings (7 and 7a). The final insertion depth is achieved when collar (9) comes into contact with the smaller of the insertion openings, i.e. opening (7a) in the posterior plate.
c) For reaming the vertebral endplate of the cranial vertebra, a rotational driving mechanism, not shown, rotates the forming tool (10) through the drive shaft (8). While the forming tool is rotating, the drive shaft (8) is moved up to the level of the upper guide channel (e.g., 5), and then it is moved along the upper guide channel. For reaming the vertebral endplate of the caudad vertebra, the process is repeated using the lower guide channel. The edge surfaces (6) of the channels (5, 5a) constrain the motion of the drive shaft (8) with attached surgical cutter or burr (10) to produce the desired milled recesses in the vertebral endplates.
d) The captive collar retains the forming tool in a perpendicular position to the guide channels and in a fixed antero-posterior (AP) position. (FIGS. 15A, 15B, 16)

Figure 15B:
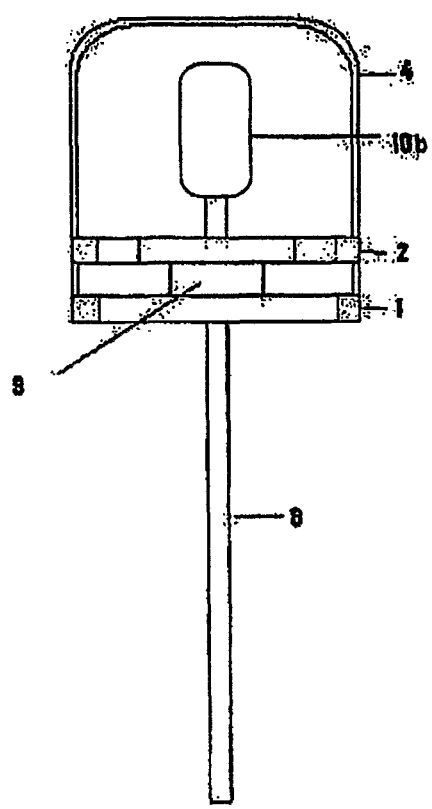
FIG. 15B is a plan view of the assembled guide frame and cutting tool of FIG. 13 wherein the surgical cutter is a cylindrical milling cutter having rounded ends.
Figure 17:
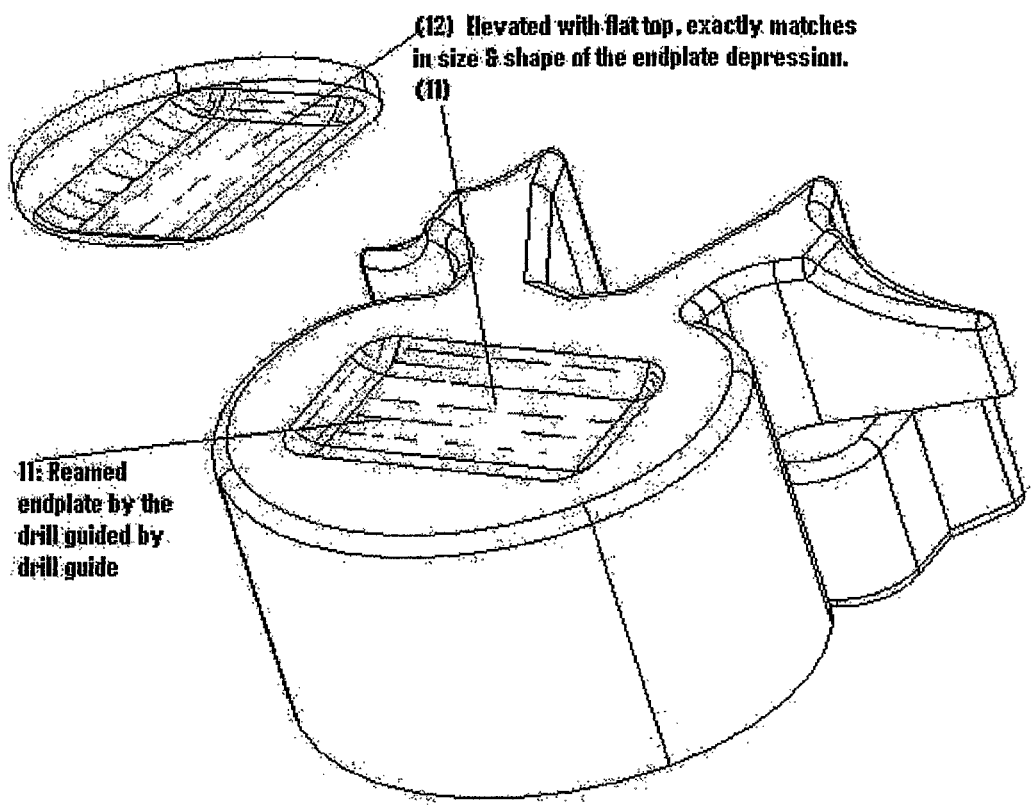
FIG. 17 illustrates a representative vertebra that has been milled by the apparatus of the invention, together with a mating endplate of an intervertebral disc replacement prosthesis.

FIG. 17 depicts an example of the form generated by the guide depicted in FIG. 15B, together with a view of the matching endplate of an intervertebral disc prosthesis. The reamed recess or depression (11) in the vertebral endplate has a specific size and shape that exactly matches the dome (12) of the endplate (e.g., a metal endplate) of the disc prosthesis.

Alternatively, the forming guide may be pre-assembled with the forming tool fully captured, as discussed above. In such an embodiment, the general configuration of the guide and tool assembly will resemble the illustrations of the assembled instrument as shown, e.g., in FIGS. 13, 14, 15, and 16, but the insertion openings will be of smaller diameter than the collar and act only to define the initial position for the forming tool, as well as to provide a connecting path between the guide channel openings. In use, such a pre-assembled unit is inserted into the disc space and the vertebral endplates are formed as described in c) above.

Preparation of Milled Recesses of Various Shapes:

The form of the recess created by the tool guide and forming tool of the invention is determined by the size and shape of the forming tool, as well as by the shape of the guide channels and their position relative to the guardrail.

Figure 18A:
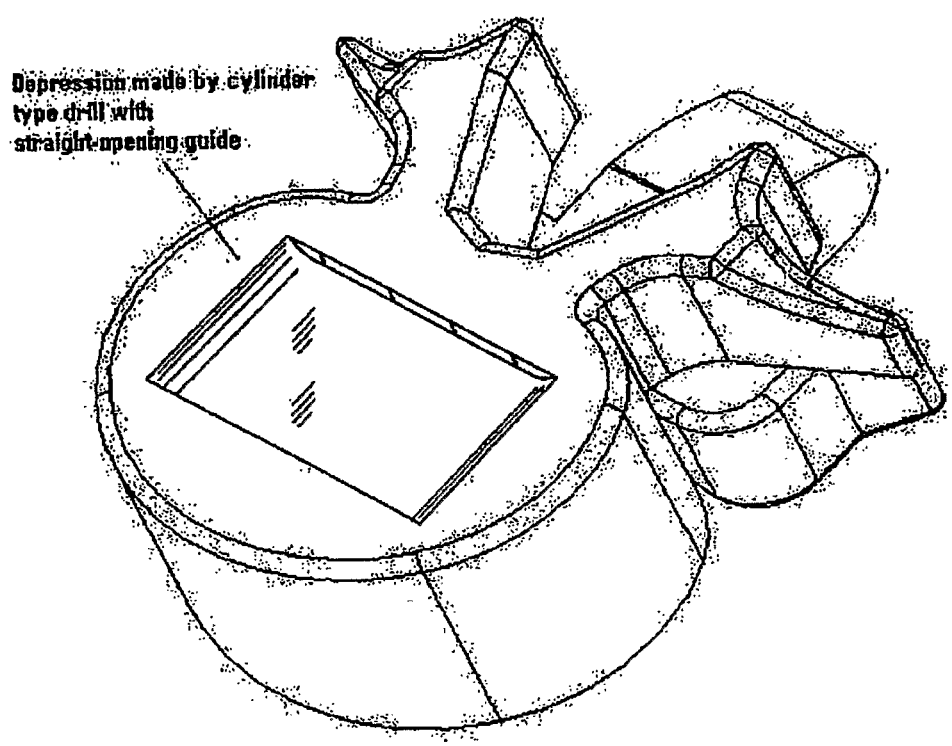
FIG. 18A illustrates a representative vertebra that has been milled by the illustrated embodiment of the apparatus of the invention, wherein the cutter used has a cylindrical shape with flat ends, as illustrated in FIGS. 15A and 22A, and the guide plates have straight guide channels, such as illustrated in FIGS. 12A and 12C.

1.) The example depicted in FIG. 18A is prepared using a cylindrical forming tool with flat ends, such as shown in FIG. 15A, following a straight line guide channel, such as shown in FIGS. 11 and 12A-12C, thereby forming a flat-bottomed, generally rectangular recess, with concave lateral sides, as illustrated.

Figure 18B:
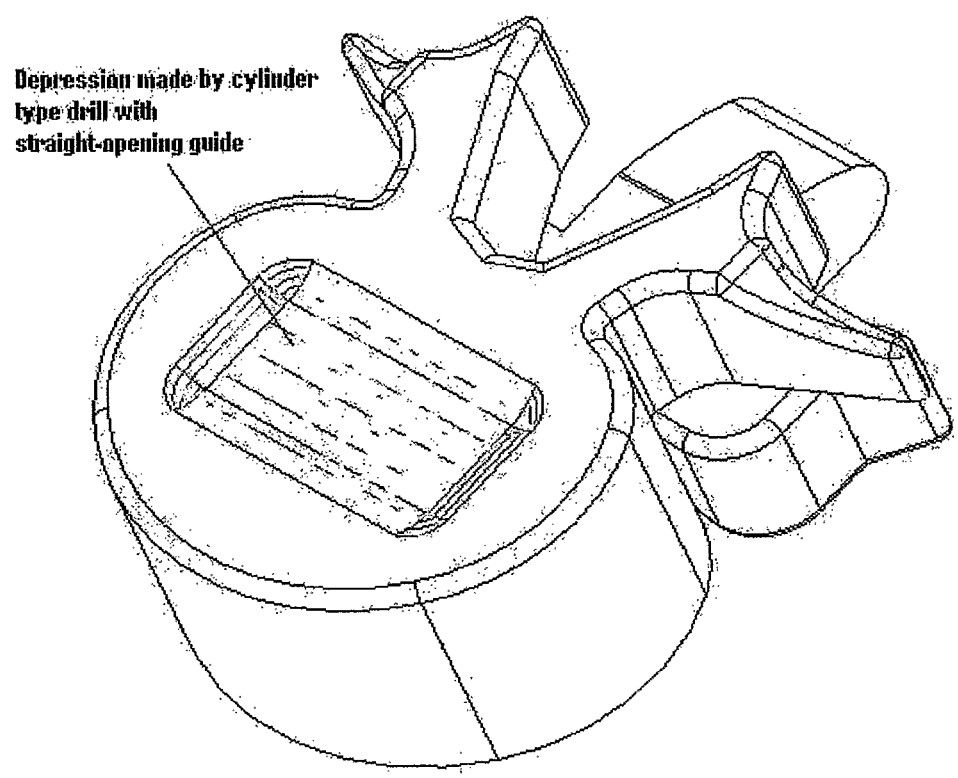
FIG. 18B illustrates a representative vertebra that has been milled by the illustrated embodiment of the apparatus of the invention, wherein the cutter used has a cylindrical shape with rounded ends, as illustrated in FIG. 15B, and the guide plates have straight guide channels, such as illustrated in FIGS. 12A and 12C.

2.) The example depicted in FIG. 18B is prepared using a cylindrical forming tool with rounded ends (10b), such as shown in FIG. 15B, following a straight line guide channel, such as shown in FIGS. 11 and 12A-12C, thereby forming a flat-bottomed, generally rectangular recess, with concave sides laterally, anteriorly, and posteriorly, as illustrated.

Figure 12A:
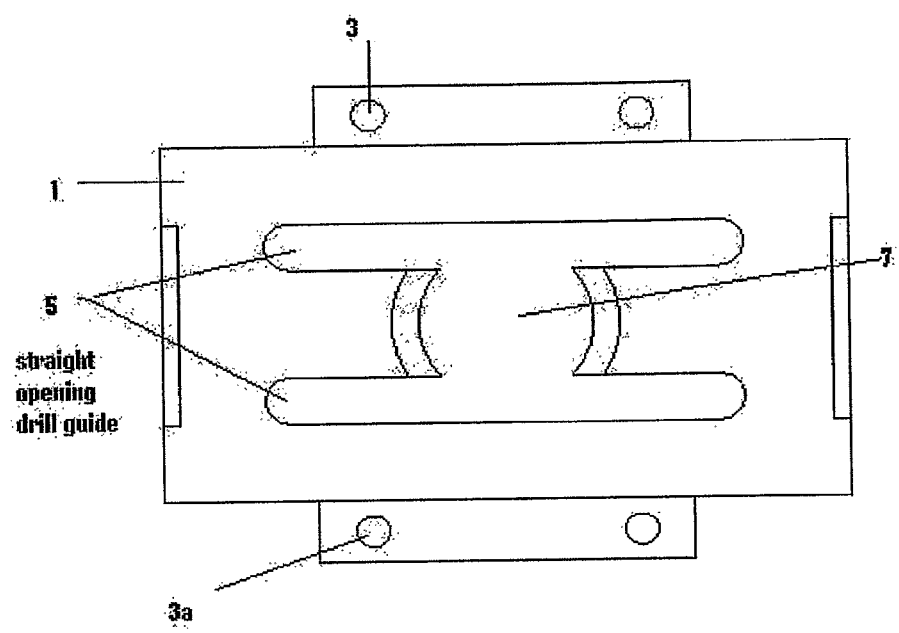
FIG. 12A is a front elevational view, in the direction indicated by numerals 12A-12A in FIG. 11, of an embodiment of the guide frame of FIG. 11 having straight guide channels.
Figure 12B:
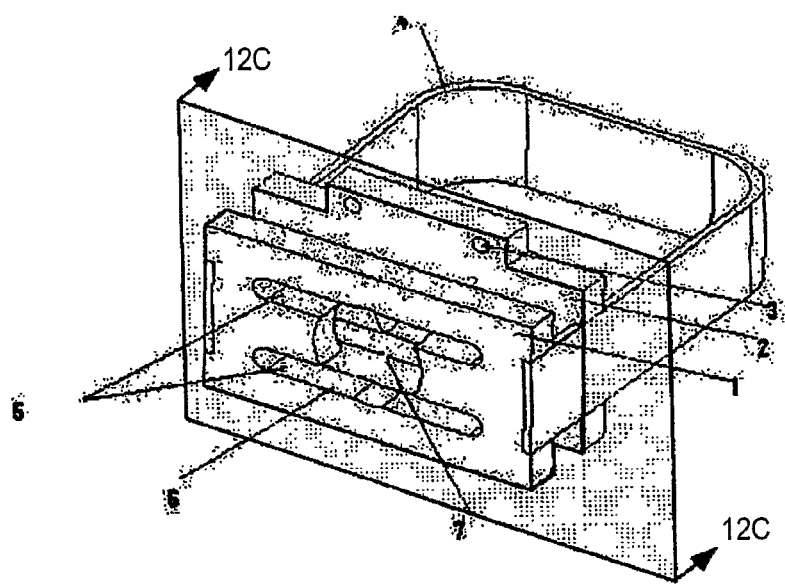
FIG. 12B is an oblique view of the guide frame of FIG. 11, showing the plane of view of FIG. 12C.
Figure 12C:
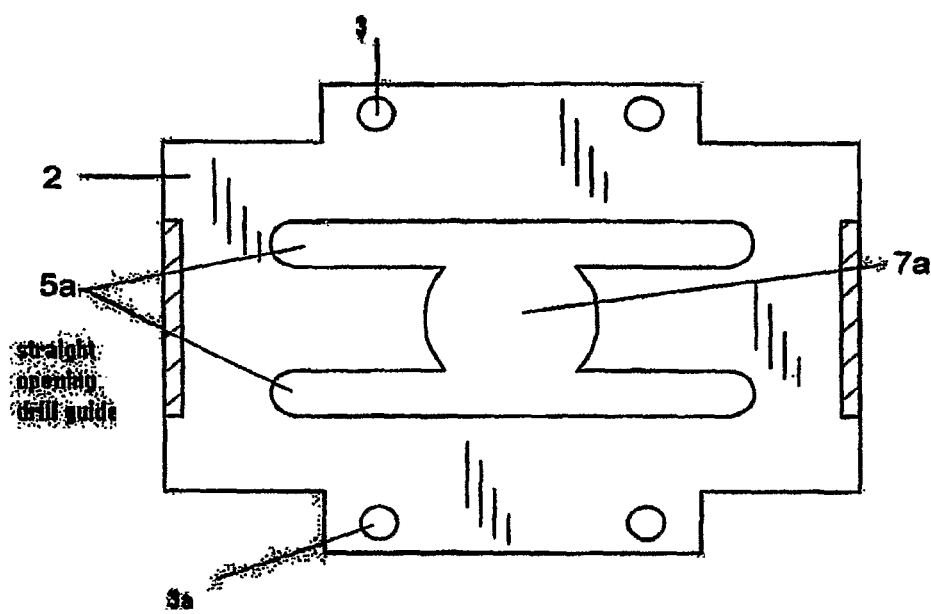
FIG. 12C is an anterior elevational cross-sectional view of the guide frame of FIG. 12B, taken at the plane 12C-12C in FIG. 12B.
Figure 12D:
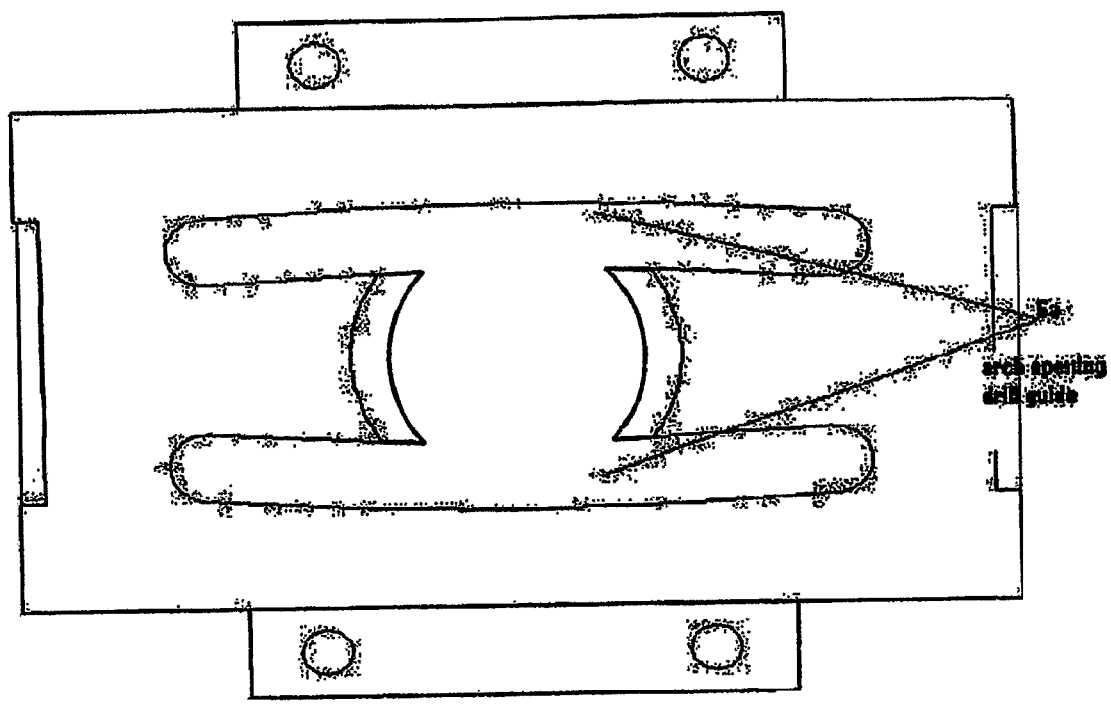
FIG. 12D is a front elevational view of an embodiment of the guide frame of the invention having curved (arched) guide channels.
Figure 13:
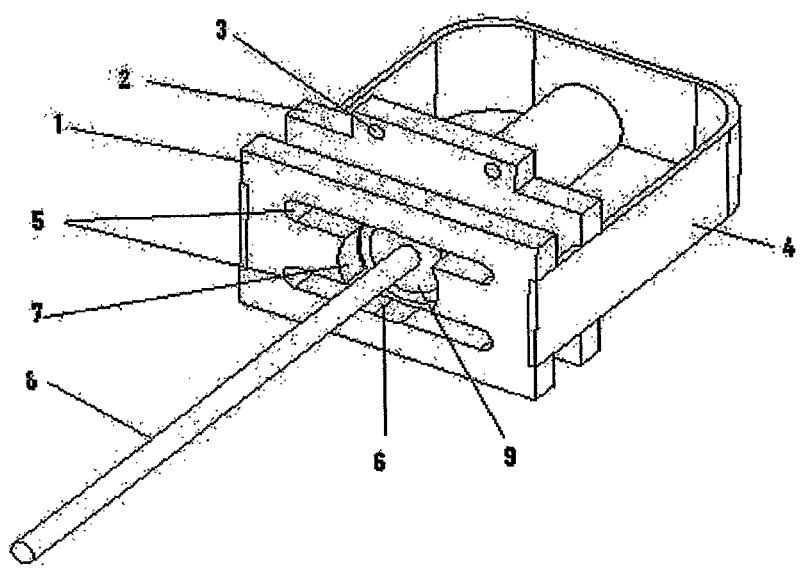
FIG. 13 is an oblique view of the embodiment of the invention illustrated in FIG. 11 showing the cutting tool inserted into the guide frame.
Figure 14:
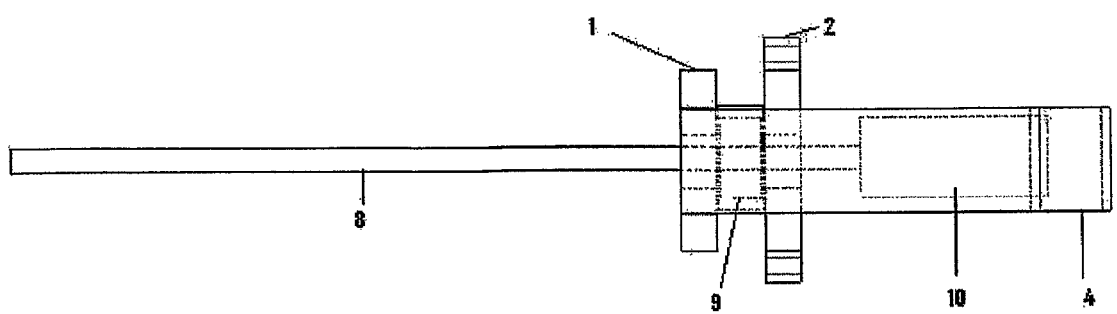
FIG. 14 is a side elevational view of the embodiment of FIG. 13, with the hidden portion of the cutting tool shown in phantom.
Figure 19A:
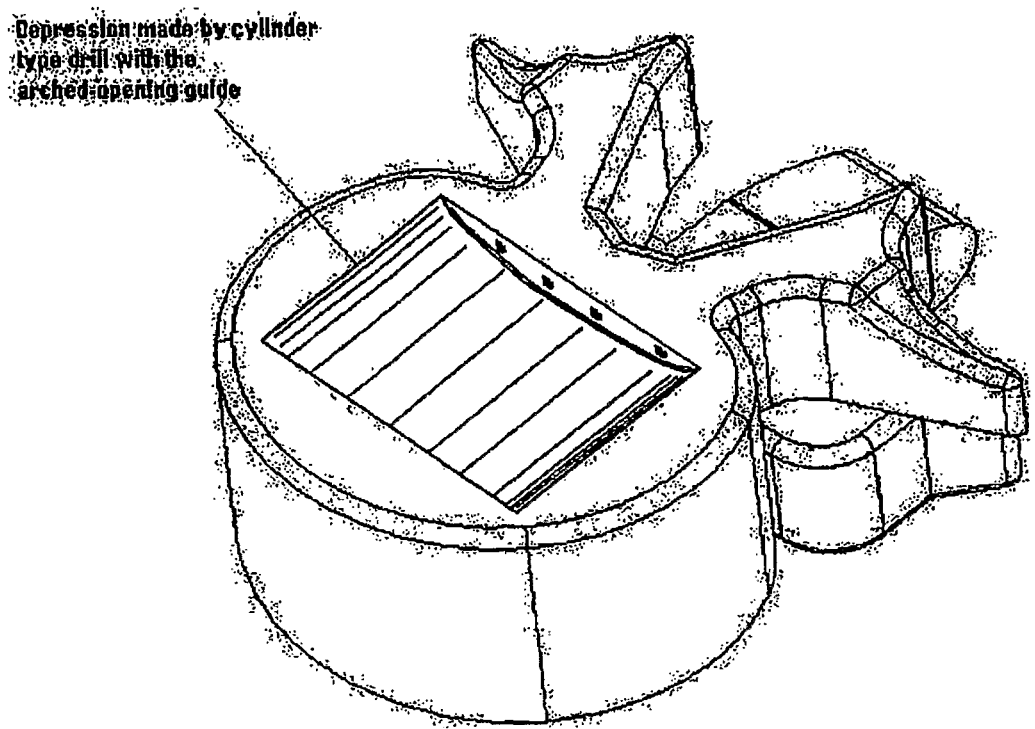
FIG. 19A illustrates a representative vertebra that has been milled by the illustrated embodiment of the apparatus of the invention, wherein the cutter used has a cylindrical shape with flat ends, as illustrated in FIGS. 15A and 22A, and the guide plates have curved guide channels, such as illustrated in FIG. 12D.

3.) The example depicted in FIG. 19A is prepared using a cylindrical forming tool with flat ends, such as shown in FIG. 15A, following a curved or arched guide channel, such as shown in FIG. 12D, thereby forming a generally cylindrical recess, with flat ends at the anterior and posterior edges, as illustrated.

Figure 19B:
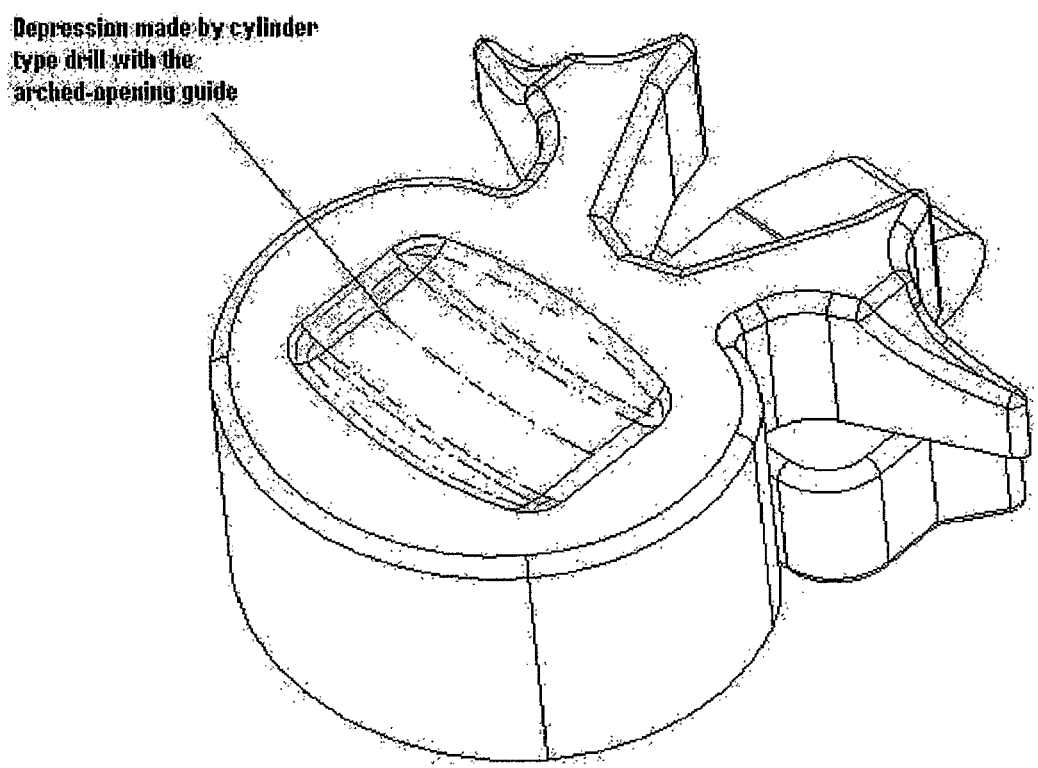
FIG. 19B illustrates a representative vertebra that has been milled by the illustrated embodiment of the apparatus of the invention, wherein the cutter used has a cylindrical shape with rounded ends, as illustrated in FIG. 15B, and the guide plates have curved guide channels, such as illustrated in FIG. 12D.
Figure 20:
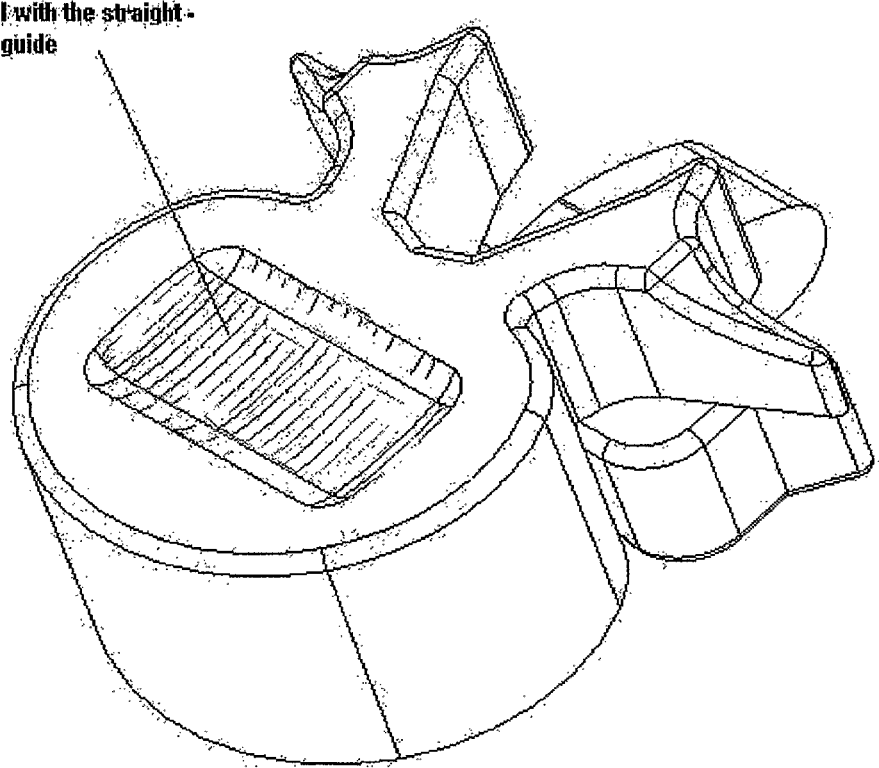
FIG. 20 illustrates a representative vertebra that has been milled by the apparatus of the invention, wherein the cutter used has a barrel-shape, such as illustrated in FIG 22B, and the guide plates have straight guide channels, such as illustrated in FIGS. 12A and 12C.
Figure 21:
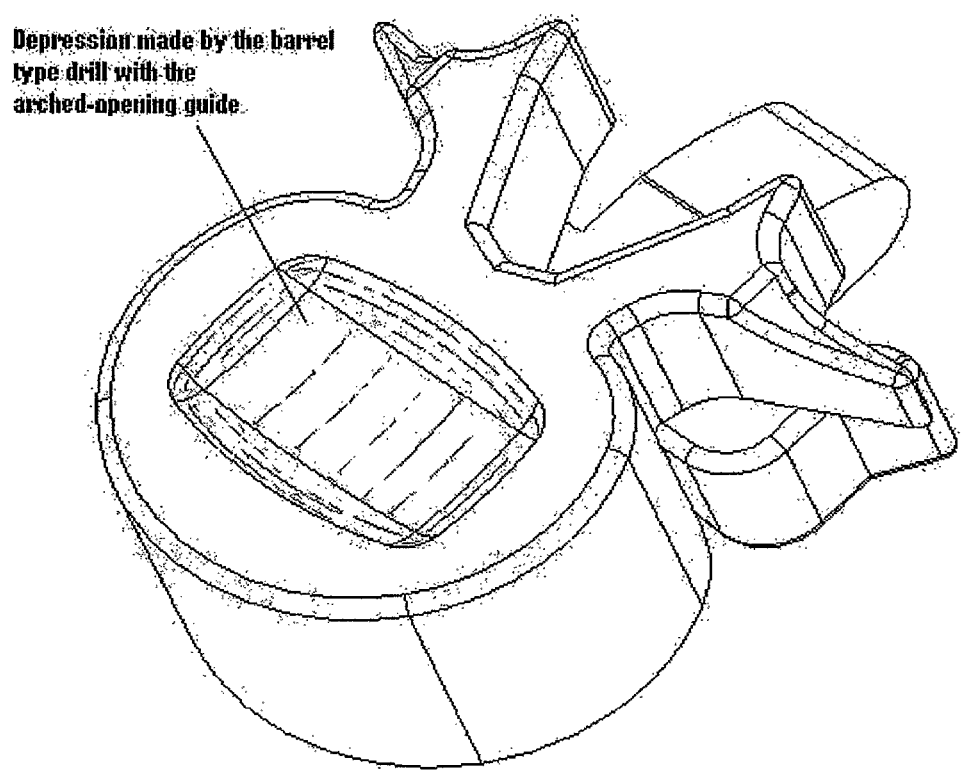
FIG. 21 illustrates a representative vertebra that has been milled by the apparatus of the invention, wherein the cutter used has a barrel-shape, such as illustrated in FIG. 22B, and the guide plates have curved guide channels, such as illustrated in FIG. 12D.

4.) The example depicted in FIG. 19B is prepared using a cylindrical forming tool with rounded ends, such as shown in FIG. 15B, following a curved guide channel, such as shown in FIG. 12D, thereby forming a generally cylindrical recess, with concave sides anteriorly and posteriorly, as illustrated.

Figure 22A:
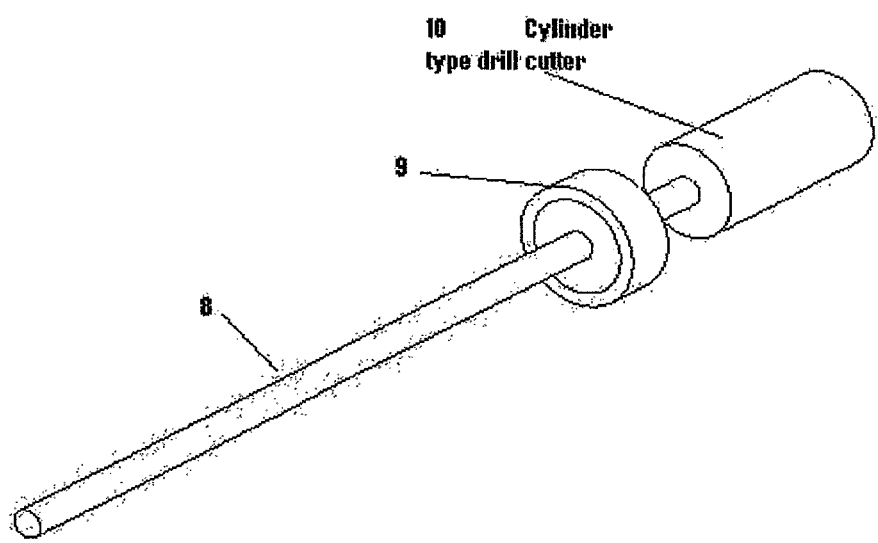
FIG. 22A illustrates a cutter assembly incorporating a cylindrical cutter with flat ends on a drive shaft with a positioning collar.
Figure 22B:
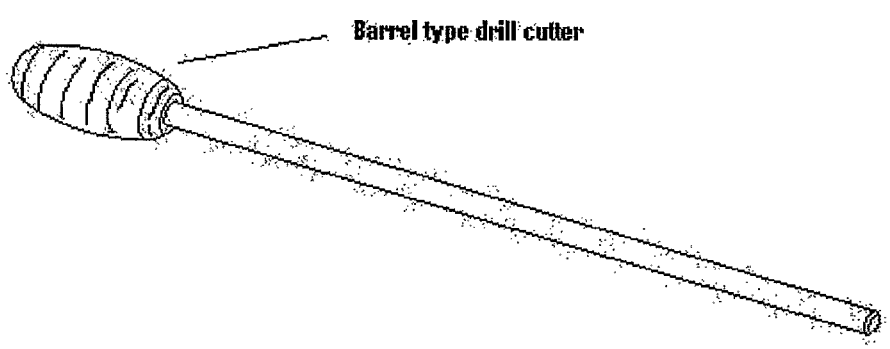
FIG. 22B illustrates a cutter assembly incorporating a barrel-shaped cutter on its drive shaft.

5.) The example depicted in FIG. 10 is prepared using a barrel-shaped forming tool with rounded ends, such as shown in FIG. 22B, following a straight line guide channel, such as shown in FIGS. 11 and 12A-12C, thereby forming a generally dome-shaped recess having concave sides and a bottom that is curved in the antero-posterior (AP) direction, but generally not curved in the lateral direction, i.e., transverse to the AP direction, as illustrated. This recess can also be considered as a cylindrical recess with its long axis positioned in a lateral direction, and having concave ends.

6.) The example depicted in FIG. 11 is prepared using a barrel-shaped forming tool with rounded ends, such as shown in FIG. 22B, following a curved guide channel, such as shown in FIG. 12D, thereby forming a generally dome-shaped recess having concave sides and a bottom that is curved in both the antero-posterior (AP) direction, and the lateral direction, i.e., transverse to the AP direction, as illustrated. The curvature of the dome is determined by the shape of the forming tool and the curvature of the guide channels.

The invention having been described in certain embodiments, it will be apparent to those skilled in the art that many changes and alterations can be made without departing from the spirit or essential characteristics of the invention. The present disclosure is therefore to be considered as illustrative, and not restrictive, of the invention.

We claim:

1. Apparatus for milling a recess in a vertebral endplate comprising:
   a surgical cutting tool including a surgical cutter and a drive shaft attached thereto, said drive shaft having a guide collar; and
   a guide frame for positioning and guiding said surgical cutter in an intervertebral space between two vertebrae adjacent along a spinal axis for milling an endplate of at least one of said vertebrae,
   said guide frame including:
      a first guide plate adapted to be fixed to at least one of said vertebrae, said guide plate having a first generally central aperture sized for admitting said drive shaft and at least one guide slot communicating with said central aperture adapted to guide said drive shaft in a predetermined path, and
      a second guide plate having a second generally central aperture sized for admitting said drive shaft and at least one guide slot communicating with said second aperture and adapted to guide said drive shaft in said predetermined path, said second guide plate being adapted to be oriented parallel to said first guide plate and spaced anteriorly therefrom by a distance selected such that said guide collar can be received between said first and second guide plates in sliding contact therewith.

2. The apparatus of claim 1, wherein said first guide plate is adapted to be fixed to both of said adjacent vertebrae.

3. The apparatus of claim 1, wherein said first generally central aperture is sized to admit said surgical cutter.

4. The apparatus of claim 1, wherein said drive shaft of said guide collar is generally cylindrical.

5. The apparatus of claim 1, wherein said first generally central aperture is sized to admit said surgical cutter but not said guide collar.

6. The apparatus of claim 1, wherein said first generally central aperture is sized to admit said surgical cutter but not said guide collar, and said second generally central aperture is sized to admit said guide collar.

7. The apparatus of claim 1, additionally comprising a guard structure extending from at least one of said guide plates adapted to extend into said intervertebral space and having a dimension parallel to said spinal axis greater than a dimension of said surgical cutter parallel to said spinal axis.

8. The apparatus of claim 7, wherein both of said first and second guide plates are attached to said guard structure.

9. The apparatus of claim 7, wherein said guard structure defines a protective space around said cutter.

10. The apparatus of claim 8, wherein said guard structure defines a protective space around said cutter.

11. A guide frame for positioning and guiding a surgical cutter in an intervertebral space between two adjacent vertebrae along a spinal axis for milling an endplate of a vertebra, said guide frame comprising:
   a generally U-shaped guard rail adapted to be inserted into said intervertebral space, said guard rail including:
      a base portion adapted to be positioned within said intervertebral space generally adjacent a posterior margin of said vertebra and having a dimension parallel with said spinal axis greater than a dimension of said surgical cutter in a direction parallel to said spinal axis, said base portion having a pair of opposite ends spaced generally a distance corresponding to a transverse diameter of said vertebra, and
      a pair of support arms extending anteriorly from said base portion, each of said support arms extending from one of said opposite ends of said base portion and terminating in a terminal end portion;
   a posterior guide plate supported on said support arms and extending between said support arms, said posterior guide plate being provided with a posterior guide plate cutter insertion aperture and at least one posterior guide plate guide channel for guiding said surgical cutter; and
   an anterior guide plate supported on said support arms and spaced anteriorly from said posterior guide plate, said anterior guide plate being provided with an anterior guide plate cutter insertion aperture and at least one anterior guide plate guide channel for guiding said surgical cutter, said posterior guide plate being spaced from said base portion of said guard rail such that said posterior guide plate is positioned generally adjacent to an anterior margin of said vertebra when said base portion of said guard rail is positioned generally adjacent said posterior margin of said vertebra.

* * * * *